(12) United States Patent
Gluschenko et al.

(10) Patent No.: US 11,096,808 B2
(45) Date of Patent: Aug. 24, 2021

(54) BIODEGRADABLE INTRAVASCULAR SHAPE MEMORY STENT

(71) Applicant: OOO "IK SOVREMENNYE TEKHNOLOGII", Ulyanovsk (RU)

(72) Inventors: Leonid Vitalyevich Gluschenko, Ulyanovsk (RU); Artur Evgenyevich Krupnin, Dubna (RU); Nikita Gennadyevich Sedush, Taganrog (RU); Vladislav Aleksandrovich Shchepochkin, Ulyanovsk (RU)

(73) Assignee: OOO "IK SOVREMENNYE TEKHNOLOGII", Ulyanovsk (RU)

( * ) Notice: Subject to any disclaimer, the term of this patent is extended or adjusted under 35 U.S.C. 154(b) by 21 days.

(21) Appl. No.: 16/616,423

(22) PCT Filed: Jul. 17, 2018

(86) PCT No.: PCT/RU2018/050079
§ 371 (c)(1),
(2) Date: Nov. 22, 2019

(87) PCT Pub. No.: WO2019/112484
PCT Pub. Date: Jun. 13, 2019

(65) Prior Publication Data
US 2020/0253760 A1    Aug. 13, 2020

(30) Foreign Application Priority Data

Dec. 7, 2017 (RU) .......................... RU2017142831

(51) Int. Cl.
*A61F 2/91* (2013.01)
*A61F 2/82* (2013.01)
(Continued)

(52) U.S. Cl.
CPC ................ *A61F 2/91* (2013.01); *A61L 27/18* (2013.01); *A61L 27/58* (2013.01); *B29C 69/001* (2013.01);
(Continued)

(58) Field of Classification Search
CPC ............. A61F 27/58; A61F 2/91; A61L 27/18
(Continued)

(56) References Cited

U.S. PATENT DOCUMENTS 6,991,647 B2    1/2006  Jadhav
8,979,921 B2 *  3/2015  Schmitz .................... A61F 2/82
                                                          623/1.42

(Continued)

OTHER PUBLICATIONS

Search Report in PCT/RU2018/050079, dated Nov. 1, 2018.

*Primary Examiner* — Suzette J Gherbi
(74) *Attorney, Agent, or Firm* — Bardmesser Law Group

(57) ABSTRACT

Biodegradable self-expanding polymer stent has an outer diameter of 0.25-40 mm, length of 5-250 mm, and closed-cell wall structure formed by struts, where ratio of inner diameter values before crimping and after crimping is in a range of 3 to 5, and made of a copolymer obtained from L-lactide, D-lactide, D,L-lactide, meso-lactide, glycolide, ε-caprolactone, trimethylene carbonate, p-dioxanone and compounds comprising functional groups capable of photopolymerization; supramolecular structure of the copolymer is oriented substantially circularly in a transversal cross section of the stent. Method of manufacturing includes extruding a tube of a polymer material; annealing the extruded polymer tube; laser cutting the extruded polymer tube to form a stent workpiece; heating the stent to above glass transition temperature of the polymer, crimping the (Continued)

stent workpiece uniformly over the entire outer surface thereof, and quenching at about minus 20 degrees Celsius; placing the quenched stent on a delivery means.

18 Claims, 16 Drawing Sheets

(51) Int. Cl.
- *A61L 27/18* (2006.01)
- *A61L 27/58* (2006.01)
- *B29C 69/00* (2006.01)
- *B29C 71/02* (2006.01)
- *B29K 67/00* (2006.01)
- *B29L 31/00* (2006.01)

(52) U.S. Cl.
CPC ...... *B29C 71/02* (2013.01); *A61F 2210/0014* (2013.01); *A61F 2240/001* (2013.01); *A61F 2250/0036* (2013.01); *A61F 2250/0037* (2013.01); *A61F 2250/0067* (2013.01); *A61F 2250/0098* (2013.01); *B29C 2071/022* (2013.01); *B29K 2067/046* (2013.01); *B29K 2995/006* (2013.01); *B29L 2031/7534* (2013.01)

(58) Field of Classification Search
USPC .............................................. 623/1.15–1.48
See application file for complete search history.

(56) References Cited

U.S. PATENT DOCUMENTS

| | | | |
|---|---|---|---|
| 10,010,436 B2 | 7/2018 | Kim | |
| 2006/0259131 A1* | 11/2006 | Molaei | A61F 2/07 623/1.44 |
| 2009/0093872 A1* | 4/2009 | Schmitz | A61L 31/16 623/1.11 |
| 2010/0131044 A1 | 5/2010 | Patel | |
| 2010/0198330 A1* | 8/2010 | Hossainy | A61F 2/91 623/1.15 |
| 2012/0041540 A1* | 2/2012 | Shobayashi | A61F 2/91 623/1.15 |
| 2014/0188243 A1* | 7/2014 | Zheng | A61L 31/06 623/23.7 |
| 2014/0296968 A1* | 10/2014 | Bader | A61F 2/07 623/1.46 |
| 2015/0305899 A1* | 10/2015 | Harrington | A61L 31/06 623/1.35 |
| 2016/0081824 A1* | 3/2016 | Harrington | B29C 65/56 29/517 |
| 2016/0213499 A1 | 7/2016 | Zheng et al. | |
| 2016/0317338 A1* | 11/2016 | Duong | A61F 2/958 |
| 2020/0405513 A1* | 12/2020 | Sirhan | A61F 2/07 |
| 2021/0007867 A1* | 1/2021 | Yan | A61F 2/915 |

* cited by examiner

| Sample | Width, mm | Thickness, mm | Distance between support points, mm | Bending stress, MPa | Bending deformation, % | Elasticity modulus, MPa | Area under curve, J | Note |
|---|---|---|---|---|---|---|---|---|
| 1 | 10.000 | 1.000 | 30.00 | 9.013 | 4.700 | 281.038 | 0.01488 | temperature 45°C |
| 2 | 10.000 | 1.000 | 30.00 | 17.396 | 4.810 | 664.267 | 0.02987 | temperature 37°C |
| 3 | 10.000 | 1.000 | 30.00 | 64.922 | 3.422 | 2984.802 | 0.11257 | temperature 22°C residual deflection 1.8 мм |

FIG. 14

BIODEGRADABLE INTRAVASCULAR SHAPE MEMORY STENT

CROSS REFERENCE TO RELATED APPLICATIONS

This application is a US National Phase of PCT/RU2018/050079, international filing date Jul. 17, 2018, which claims priority to Russian Patent Application No. 2017142831, filed Dec. 7, 2017, which are both incorporated herein by reference in their entirety.

FIELD OF THE INVENTION

The invention relates to biodegradable endovascular shape memory stents, which may be deployed without use of expanding balloons or any other expanding means.

BACKGROUND OF THE RELATED ART

Endovascular stents are used for treatment of atherosclerotic lesions, radiation damages, posttraumatic effects, etc., which cause a hemodynamically sufficient arteriostenosis or arterial occlusive disease. A decrease in the number of restenosis cases and maintaining a vessel lumen open are ensured by stent biodegradation defined by a presence of links in molecular structure of a stent material, which are subject to degrade, by stent geometric characteristics, and by implantation site. A decrease in number of thrombosis cases is ensured by tight engagement between a stent and a vascular wall and by an absence of recoil owing to a shape memory effect. Use of shape memory stents allows avoiding use of expanding means, in particular, expanding balloons, which makes the stent deployment procedure easier and improves physioanatomical properties of the vessel after stent deployment. In particular, it allows physiological arterial contractions necessary for full vessel functioning. Moreover, shape memory stents are able to be shaped according to tortuous vessels, which is impossible when balloon-expandable stents are used.

Currently, the non-balloon technology of stent deployment is available for metal shape memory stents only. However, temporal characteristics of biological degradation of such stents do not always meet requirements; in addition, after-effects of such stent deployment inside an organism may not be acceptable for all patients.

According to recent progress in biodegradable polymer structural materials, researchers have paid their attention to biodegradable endovascular shape memory polymer stents, which fact is attested by a substantial number of patent and non-patent documents of the past two decades.

Patent publications US2007132155A1, US2007135899, US2007134289A1, CA2570890A1, CA2571128A1, CA2571141A1, CA2571152A1, CA2571157A1, CA2571193A1, CA2579477A1, CA2590310A1, CA2590318A1 CA2590355A1, CA2579250A1 disclose a biodegradable self-expanding stent made of a polymer material, with a one-layer configuration of struts in its wall. A drawback of this stent is a low radial force due to a non-optimal configuration of struts.

Patent publication US2009035350A1 discloses a biodegradable self-expanding stent made of a polymer material, in which an attempt was made to improve its mechanical properties by use of two or more segments made of materials having different glass transition temperature values. This document does not disclose the stent configuration; therefore, the effectiveness of such an approach remains unclear.

Patent publications US20090182404A1, US20100016940A1 disclose a biodegradable self-expanding stent made of a polymer material, having a drawback related to webbed arrangement of its wall, which decreases operational lumen diameter of a vessel.

Patent publications WO2010135433A1, WO2013158619A2 disclose a biodegradable self-expanding stent made of a polymer material, having a drawback related to webbed arrangement of its wall, which decreases operational lumen diameter of a vessel.

Patent publication CA2822321A1 discloses a biodegradable self-expanding stent made of a polymer material, in which an attempt was made to improve its mechanical properties by use of two-layer wall, wherein one layer forms a frame and the other layer forms a fine mesh. However, the mesh has a limited elasticity, which impedes full opening of the stent; in addition, use of the two-layer wall makes production technology more complicated and imposes some restrictions on stent applications.

Patent publications US2012271396A1, WO2013003644A1 disclose a biodegradable self-expanding stent made of a polymer material, having a single-layer arrangement of struts in its wall; its drawback is a low radial force due to a non-optimal configuration of struts.

Patent publication US20140090231A1 discloses a biodegradable stent made of a polymer material, in which some portions of struts have a reduced width compared to the other portions, in order to provide increased flexibility and to reduce damage during crimping and deployment. However, this stent requires using a balloon during its deployment.

Patent publications WO2015112915A1, US2016213499A1 disclose a biodegradable self-expanding stent made of a polymer material, having a single-layer arrangement of struts in its wall; its drawback is a low radial force due to a non-optimal configuration of struts.

Patent publication US2015359647A1 discloses a biodegradable self-expanding stent made of a polymer material, having a single-layer arrangement of struts in its wall; its drawback is a low radial force due to a non-optimal configuration of struts.

Publication [1] discloses using co-polymers PCTBV containing poly(εocaprolactone) (PCL) for manufacturing biodegradable self-expanding stents.

Publication [2] discloses using oligo(ε-caprolactone) (bOCL) for manufacturing medical devices.

Publication [3] discloses using shape memory polymer materials for manufacturing biodegradable cardiovascular stents.

Publication [4] discloses using shape memory polymer materials for manufacturing various devices, including medical devices.

Publication [5] discloses using poly(lactide acid)-based shape memory polymer materials, including biodegradable materials for medical use.

Publication [6] discloses obtaining shape memory polymer materials based on poly-1-lactic acid (PLLA), including biodegradable materials for medical use.

Publication [7] discloses use of shape memory polymer materials, wherein p-dioxanone, diglycolide or ε-caprolactone is used for synthesis of co-polymers for manufacturing biodegradable materials for medical use.

Publication [8] discloses effect of structure and length of crystallite structures of segmented poly(ε-caprolactone) polyurethanes derived from poly(ε-caprolactone)diol on shape memory properties.

Publication [9] discloses use of moisture-sensitive chitosan polyester structures for manufacturing biodegradable stents.

Publication [10] discloses use of L-lactide, glycolide and trimethylene carbonate terpolymers capable of restoring their shape at a body temperature for manufacturing biodegradable medical devices.

Publication [11] discloses use of shape memory polymer materials based on oligo(ε-caprolactone)diol for manufacturing biodegradable medical devices.

Publication [12] discloses use of shape memory polymer materials based on poly(ε-caprolactone)dimethacrylate for in vivo applications.

Publication [13] discloses thermal and mechanical properties of copolymers based on lactides like poly(lactide-co-glycolide) (PLGA), poly(lactide-co-p-dioxanone) (PLDON) and poly(lactide-co-caprolactone) (PLC), which are appropriate for manufacturing biodegradable self-expanding stents.

Publication [14] discloses thermal and mechanical properties of copolymers based on PEG-PCL in comparison with PEG/E-CL.

Publication [15] discloses use of poly(ε-caprolactone-co-DL-lactide) having shape memory properties for manufacturing biodegradable stents.

Publication [16] discloses use of radiological properties of materials based on poly(ε-caprolactone) applicable for manufacturing biodegradable stents.

Publication [17] discloses use of poly(ε-caprolactone) having shape memory properties for manufacturing biodegradable stents.

Publication [18] discloses use of poly(lactide-co-glycolide) (PLGA) and poly(L-lactic acid) (PLLA) having shape memory properties for manufacturing biodegradable stents.

Publication [19] discloses use of poly(ε-caprolactone) (PCL) having shape memory properties for manufacturing biodegradable stents.

Publication [20] discloses use of materials based on poly(ε-caprolactone) (cPCL) and poly(sebacic anhydride) (PSA) for manufacturing biodegradable medical devices.

However, the problem of development of shape memory polymer stents having acceptable combination of mechanical, biochemical and technological characteristics turned to be non-trivial and such stents have not been produced so far.

Thus, the problem of providing biodegradable shape memory polymer stents having improved combination of mechanical, biochemical and technological characteristics is still highly relevant.

SUMMARY OF THE INVENTION

An object of this invention is providing a range of biodegradable shape memory stents of different sizes, which would have improved combination of mechanical, biochemical and technological characteristics, which configuration and production technology would be suitable for mass production.

This object is achieved by providing a biodegradable shape memory stent made of a polymer, where struts form a closed-cell structure.

A ratio of inner diameter values before crimping and after crimping may be in a range of 3-5 for such a stent. This allows placing reduced stents having various purposes into delivery means applicable for implantation of the stents in various vessels, ducts, etc. Outer diameter of the stent may be in a range of approximately 0.25 mm to approximately 40 mm, depending on the stent purpose, while its length may be in a range of 5-250 mm, depending on the stent purpose.

The average molecular weight of a polymer for manufacturing the stent may be 20-600 kDa, preferably 100-400 kDa, and its polydispersity index may be 1.3-2.5, preferably 1.5-2.0. The polymer may have a main glass transition temperature over 37 degrees Celsius, preferably over 42 degrees Celsius.

The polymer may be obtained by copolymerization of monomers selected from the following group: L-lactide, D-lactide, D,L-lactide, meso-lactide, glycolide, ε-caprolactone, trimethylene carbonate, p-dioxanone and compounds comprising functional groups capable of photopolymerization. In particular, the polymer may be a copolymer of L,L-lactide and ε-caprolactone.

Width of struts may be 0.01 mm to 1 mm, while thickness of struts may be 0.02 mm to 0.5 mm, depending on stent diameter.

Struts before crimping may have a substantially sinusoidal shape and their width may be increased in places of maximum mechanical stress that occurs during production and/or during operation of the stent. Also, struts may have decreased thickness and/or openings in places of minimum mechanical stress that occurs during production or during operation of the stent.

Crystallite structures of the polymer may be oriented substantially circularly, when seen in transversal cross section of the stent.

The aim of the invention is also achieved by providing a method of manufacturing a biodegradable self-expanding stent, the method comprising the following steps:

extruding a tube of a polymer material, while the extrusion may be performed so as crystallite structures of the polymer have a substantially circular orientation, when seen in transversal cross section of the tube;

annealing the extruded polymer tube;

laser cutting the extruded polymer tube to form a stent workpiece, wherein struts form a closed-cell structure and may have a substantially sinusoidal shape prior to crimping;

heating the stent workpiece to a temperature over glass transition temperature of the polymer material, sharply crimping the stent workpiece uniformly over crimping thereof, and subsequently rapidly cooling (quenching) the stent workpiece down to temperature of minus 20 degrees Celsius or a lower temperature;

placing the quenched stent on/in a delivery means;

performing packing, marking and sterilization.

A technical result attaining by the claimed invention is providing possibility of manufacturing a range of shape memory stents having various sizes and improved combination of mechanical, biochemical and technological characteristics, which configuration and production technology are suitable for mass production.

The closed shape of the struts assures a ratio of the stent inner diameter values before crimping and after crimping to be in a range of 1:3-5, which allows manufacturing stents in a wide size range and covering a wide range of the stent purposes. Moreover, such a shape also allows providing increased force during expansion phase owing to shape memory effect and improved load-carry capability of the stent after its deployment in situ. In addition, the closed shape of struts allows providing increased width of struts in places of maximum mechanical stress that occurs during production and/or during operation of the stent, which also improves mechanical properties of the stent. Sinusoidal or near-sinusoidal shape of struts is close to optimal shape in the light of ensuring the above-indicated properties of the stent.

Reduced thickness and/or presence of openings in places of minimum mechanical stress that occurs during manufacturing and/or during operation of the stent allows equalizing mechanical stress in the stent material and ensuring more even and predictable degradation of the stent material, which reduces risk of detachment and migration of strut fragments along blood channels.

Average molecular weight of a polymer for manufacturing the stent and its polydispersity index in the claimed value range provide the necessary temporal characteristics during operations of the stent inside an organism, including a time period, when its mechanical properties are maintained at an acceptable level, and a time period for its full decomposition.

The substantially circular orientation of the polymer crystallite structures, when seen in transversal cross section of the stent, facilitates improving its mechanical properties, in particular, increased force generated by the stent during its deployment and advanced load-carry capability of the stent after its implantation.

BRIEF DESCRIPTION OF THE ATTACHED DRAWINGS

FIG. 14 shows measurement results for mechanical properties of a polymer used in a stent according to the invention, depending on temperature.

Figure 15:
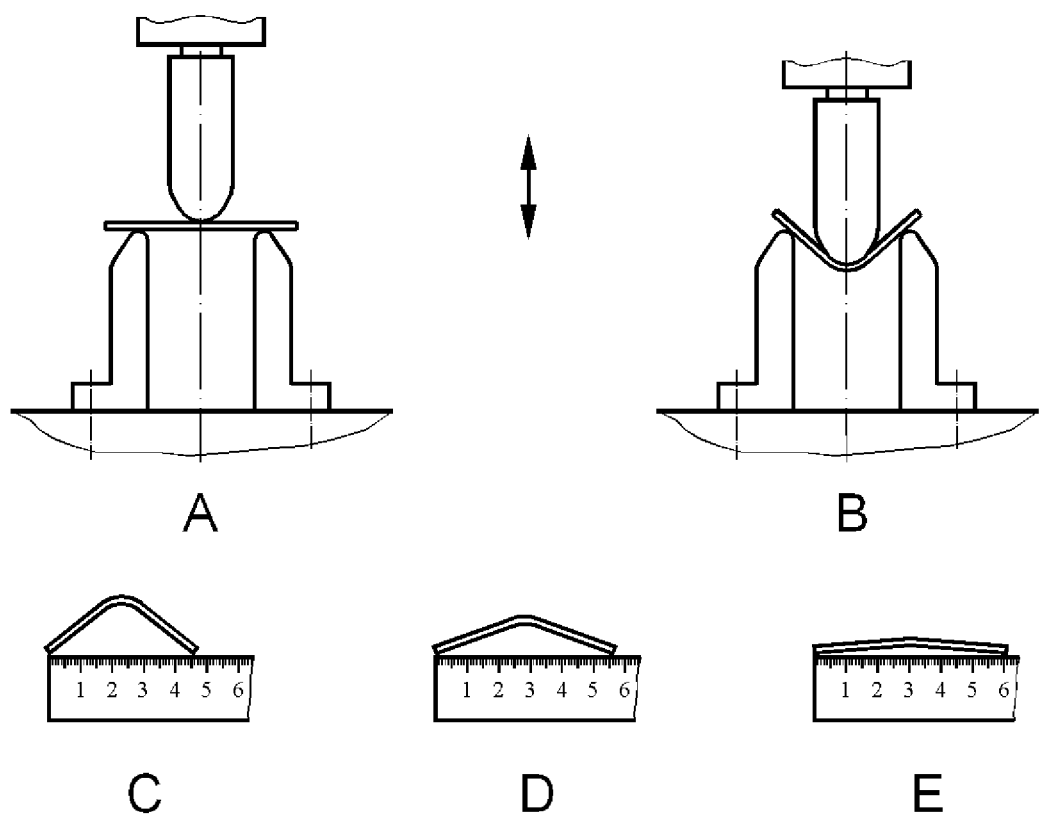

FIG. 15, part A shows a test setup before a sample was deformed, the sample made of a polymer used in a stent according to the invention.

FIG. 15, part B shows a test setup after a sample was deformed, the sample made of a polymer used in a stent according to the invention.

FIG. 15, part C shows a shape of a sample made of a polymer used in a stent according to the invention, right after quenching.

FIG. 15, part D shows a shape of a sample made of a polymer used in a stent according to the invention, after exposition for 1.5 hours at a room temperature.

FIG. 15, part E shows a shape of a sample made of a polymer used in a stent according to the invention, after the test was over.

Figure 16:
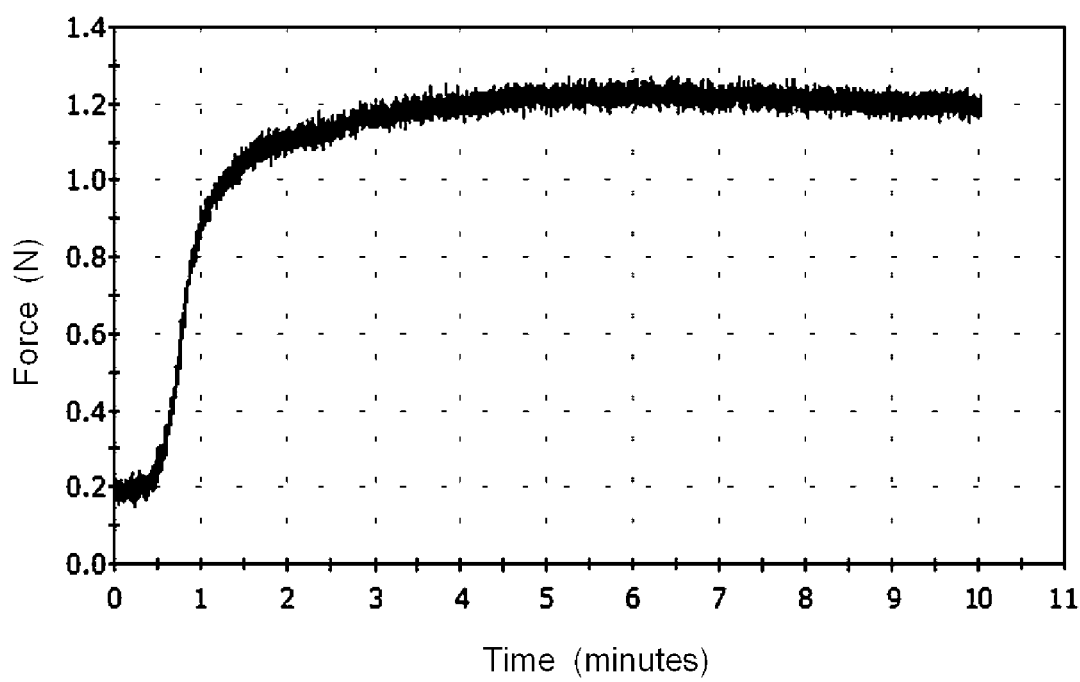

FIG. 16 shows a diagram of change in time of strength force of a sample made of a polymer used in a stent according to the invention, with a constant deformation during heating up a test chamber.

Figure 17:
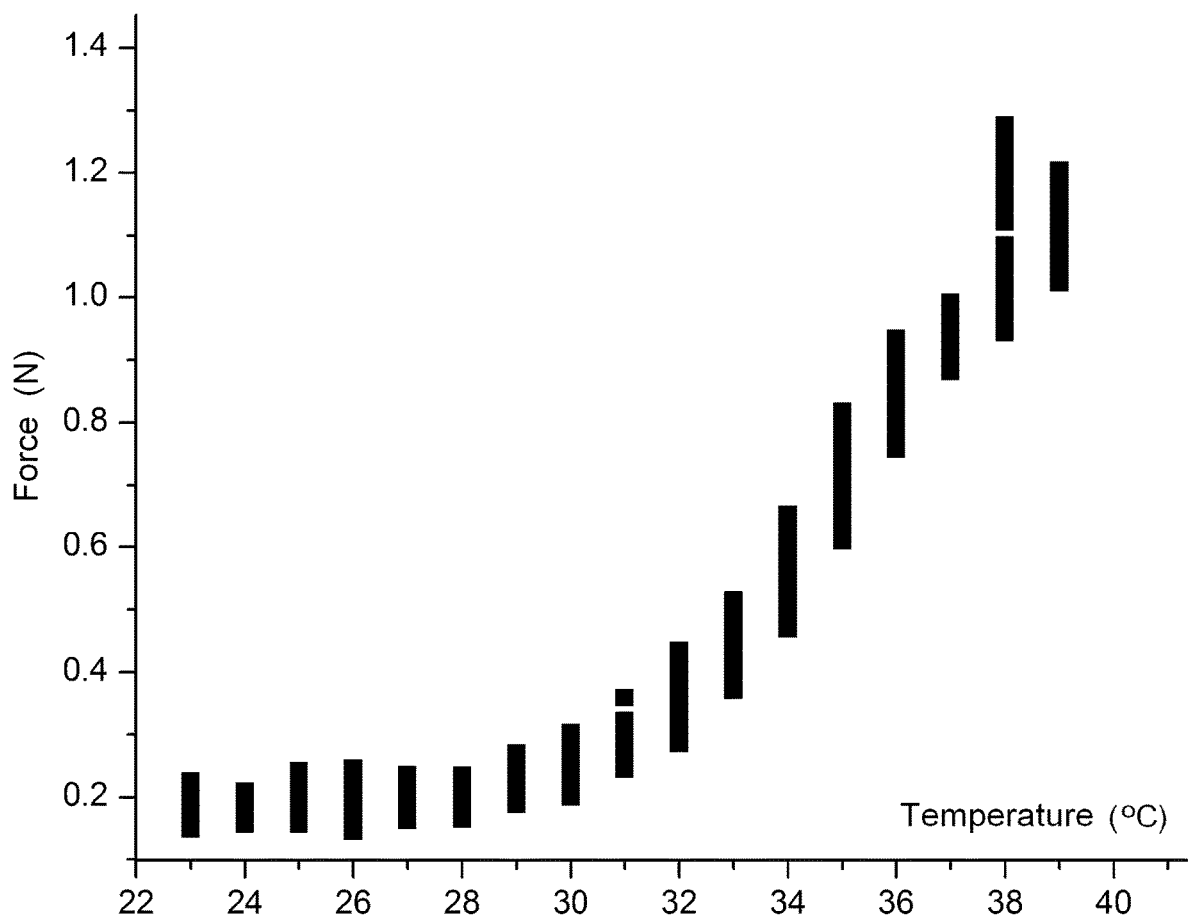

FIG. 17 shows a diagram of strength force of a sample made of a polymer used in a stent according to the invention, with a constant deformation, depending on temperature.

Figure 18:
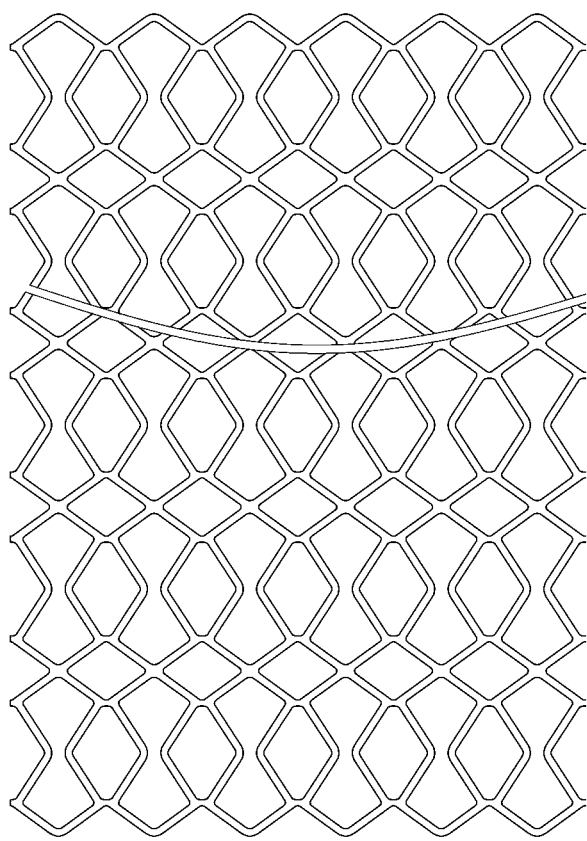

FIG. 18 shows a flattened view of another pattern of stent struts, according to the invention.

Figure 19:
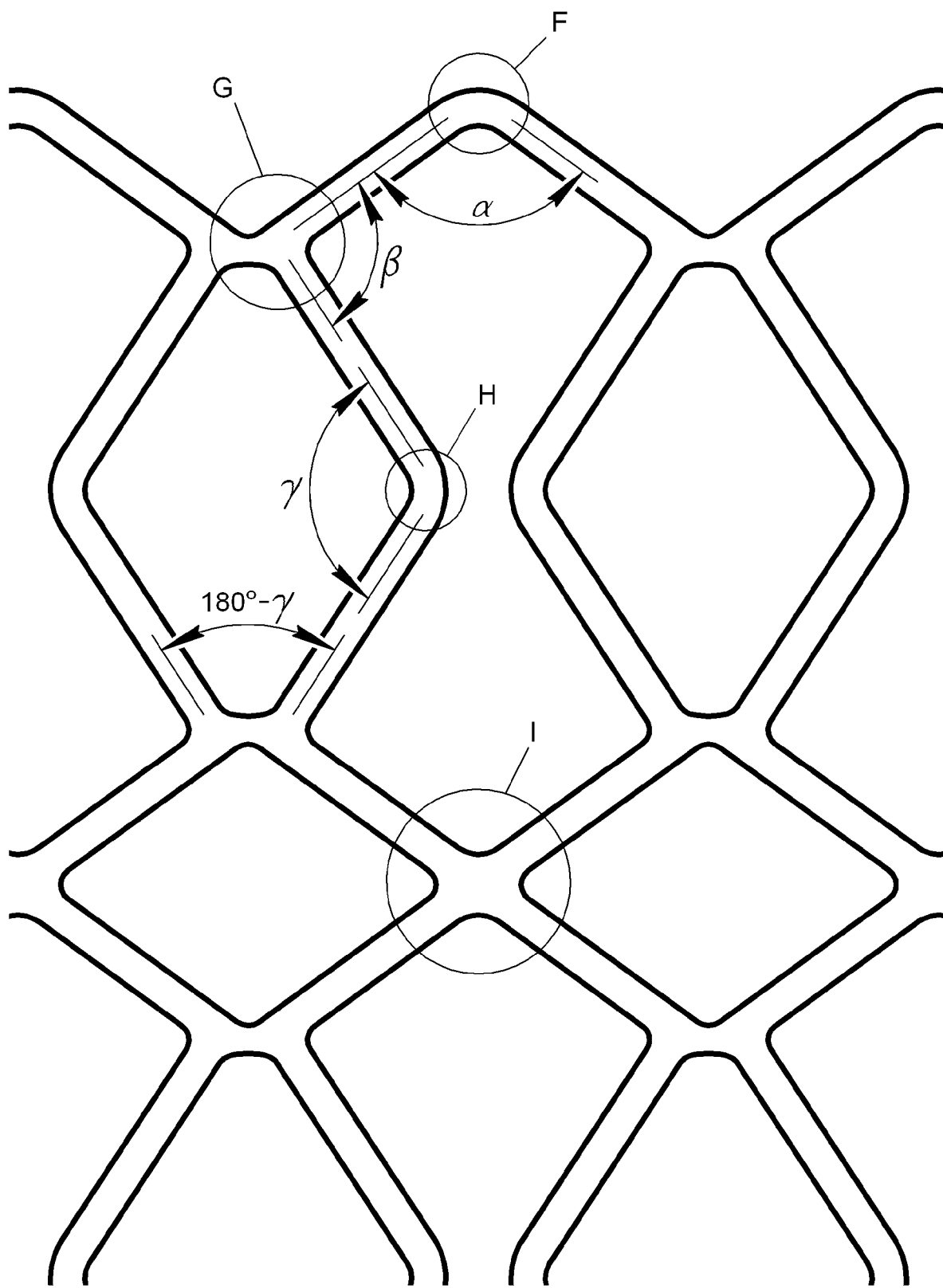

FIG. 19 shows an enlarged cell view of another pattern, according to the invention.

Figure 20:
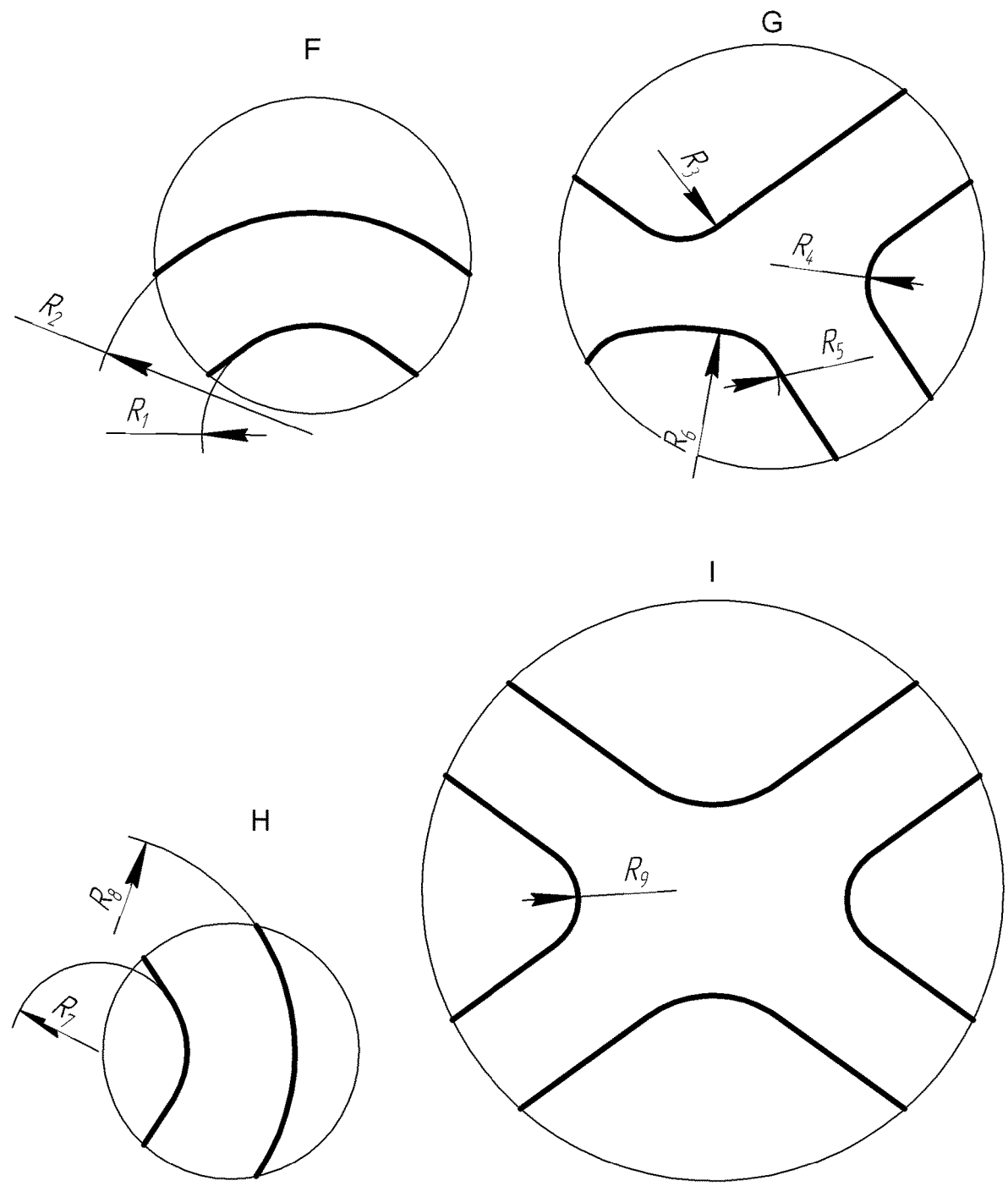

FIG. 20 shows details of the cell of FIG. 19.

Figure 1:
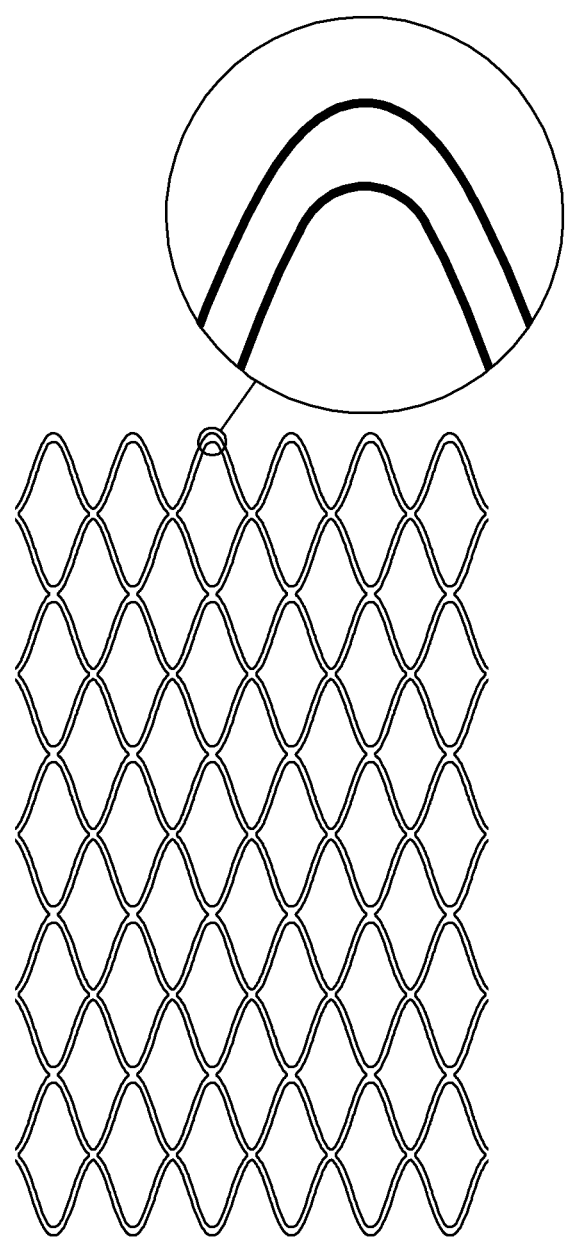
FIG. 1 shows a pattern of stent struts, according to the invention.
Figure 21:
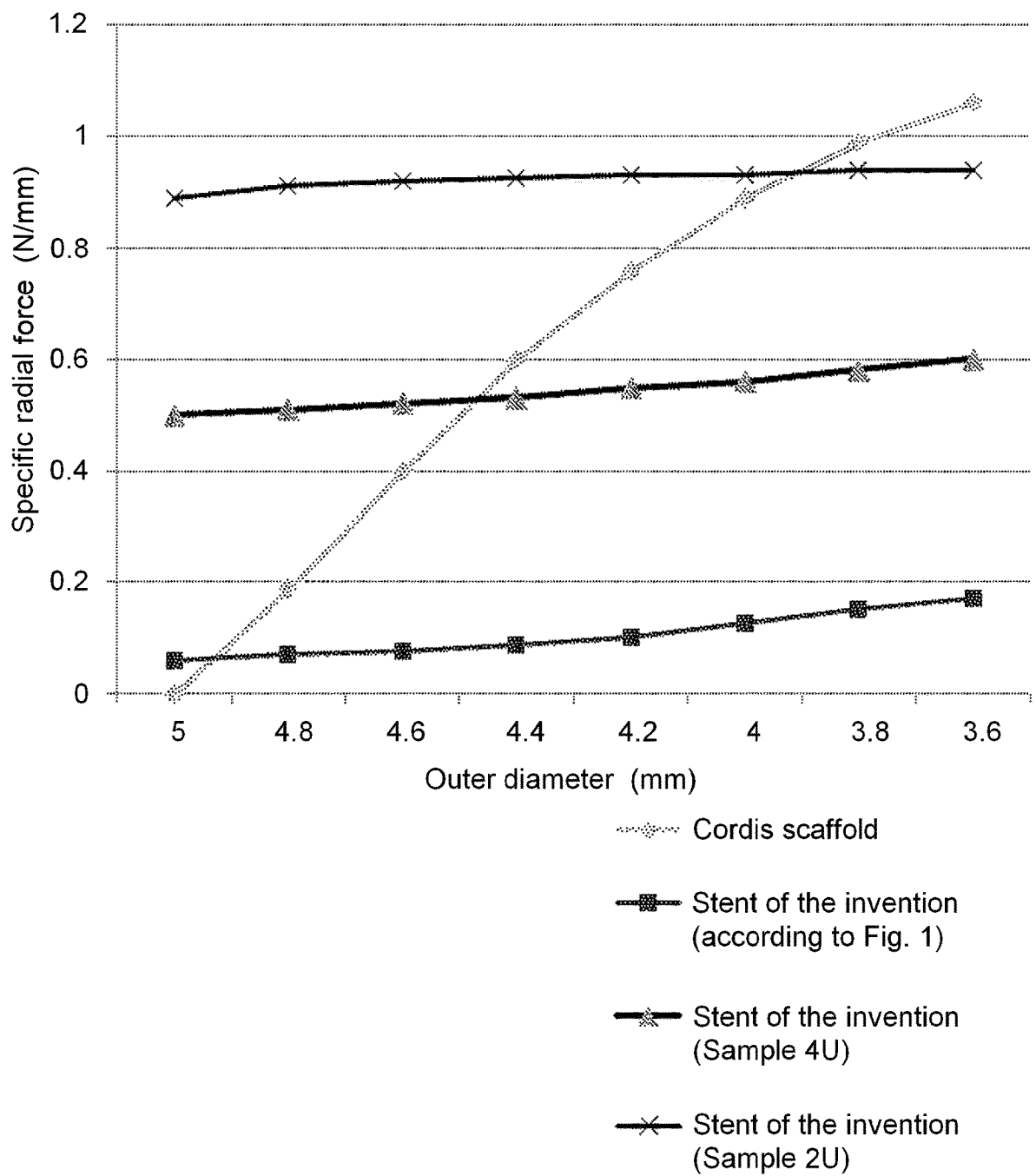

FIG. 21 shows a relative force value generated by stents having strut patterns of FIG. 1, FIG. 18 and by a reference sample of a metal stent, depending on outer diameter.

Figure 22:
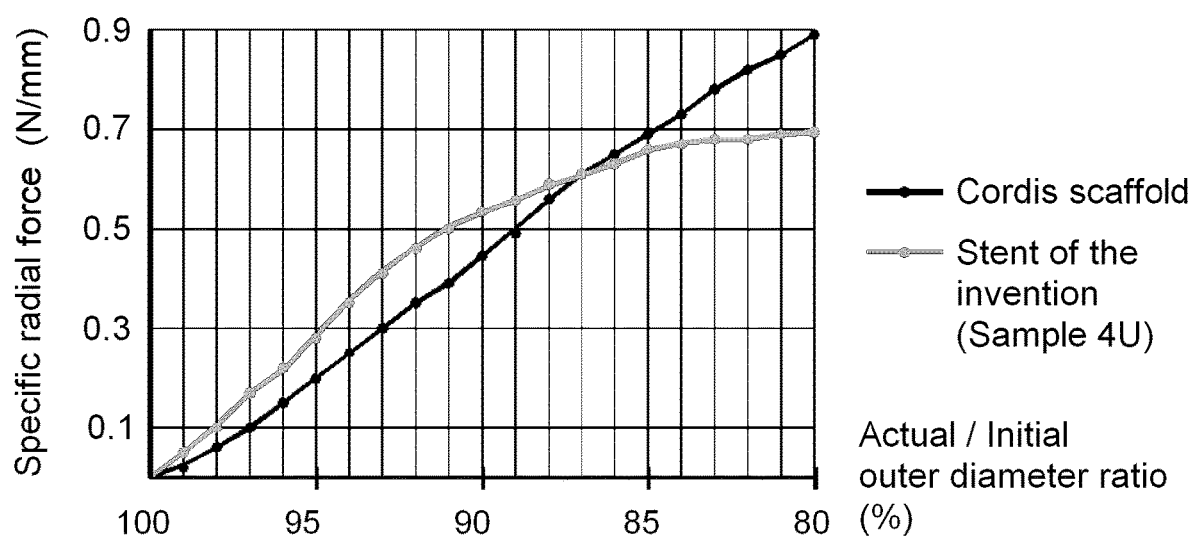

FIG. 22 shows a relative radial force generated by a stent having strut pattern of FIG. 18 and by a reference sample of a metal stent depending on ratio of actual outer diameter after deployment and initial outer diameter.

DETAILED DESCRIPTION OF EMBODIMENTS OF THE INVENTION

Configuration and Dimensions

The shape of a stent is defined by anatomy features of vessels into which the stent is implanted. Usually, stents are shaped as hollow cylinders. However, a stent may be shaped differently, e.g., as a hollow truncated cone. When a stent is deployed in places of branching or joining vessels, its walls may have openings for passing a flow of blood or another fluid.

FIG. 1 shows one option of a flattened pattern of stent struts. The stent wall is formed by a closed-cell structure. Closed cells provide a higher radial rigidity of the stent. Struts have thickened portions in places of maximum concentration of mechanical stress (e.g., see the enlarged spot in FIG. 1). This arrangement ensures improved strength of the stent and enables the stent to withstand a single-shot load (applied once during crimping) and recurrent loads (applied many times due to contraction of vessel walls). Therefore, this arrangement reduces the probability of occurrence of micro cracks in the material of struts and, correspondingly, prevents early destruction of struts, which would cause a risk of detachment and migration of strut fragments along blood vessels, and allows more uniform and predictable stent degradation. Additionally, this arrangement increases a contact area between the stent and the vessel walls, which reduces the probability and distance of migration of the entire stent along the vascular channel.

Figure 2:
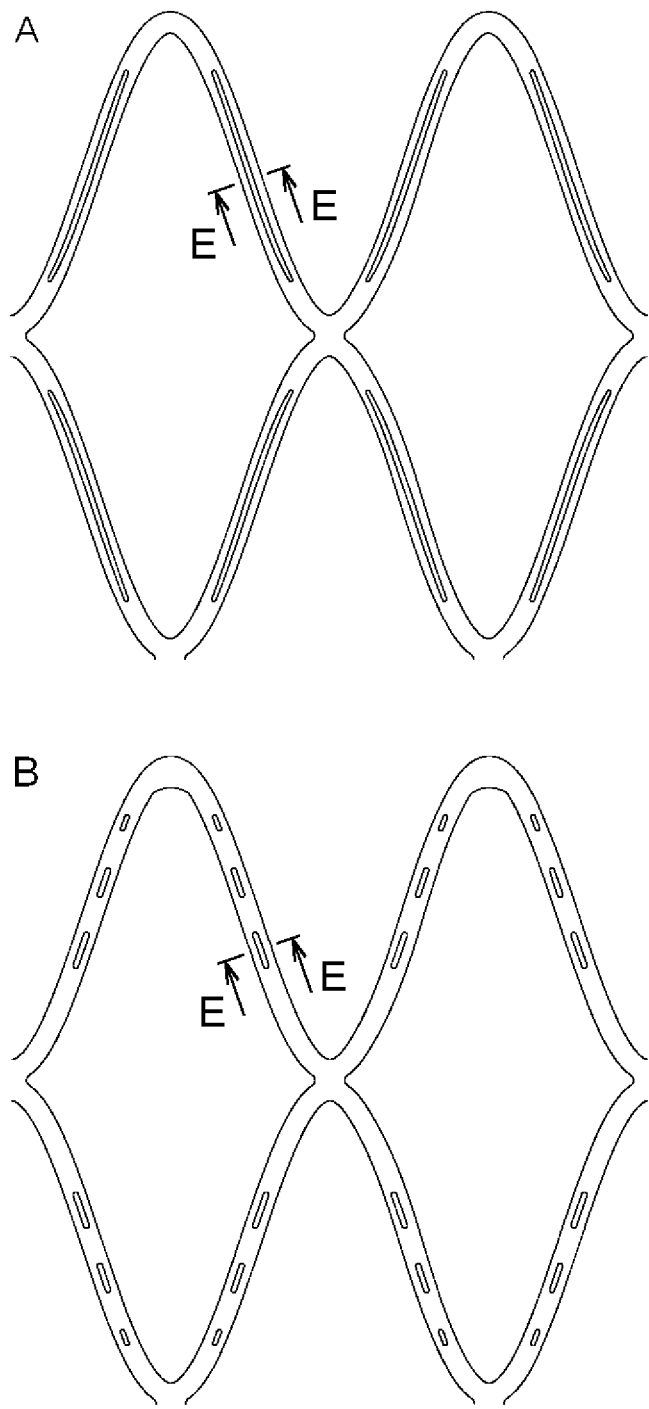
FIG. 2 shows options of stent strut implementations (configurations), according to the invention.

FIG. 2 shows options of configuration of struts. It is known that the degradation rate of polymer stents depends on a concentration of mechanical stress in the stent material. The stress results from external forces and deformations caused by these forces. Calculations indicate that low (down to zero values) stress areas are located in the middle portions of struts along their symmetry axis, where the stress occurs due to crimping (reducing) the stent during its manufacturing process and due to exposure to a radial load during its operation. This means that the structure is underloaded in these areas. In order to ensure more even distribution of the stress and, therefore, to provide uniform degradation of the stent, struts may have perforated or thinned (recessed) regions in the above-mentioned low stress areas. The perforated or thinned regions may be shaped to various geometric figures and combinations thereof, including elongated (e.g., as shown in FIG. 2, part A) or compact (e.g., as shown in FIG. 2, part B), straight or curved figures. The openings (elongated perforations) and recessed regions may be combined in a strut, e.g., they may alternate.

Figure 3:
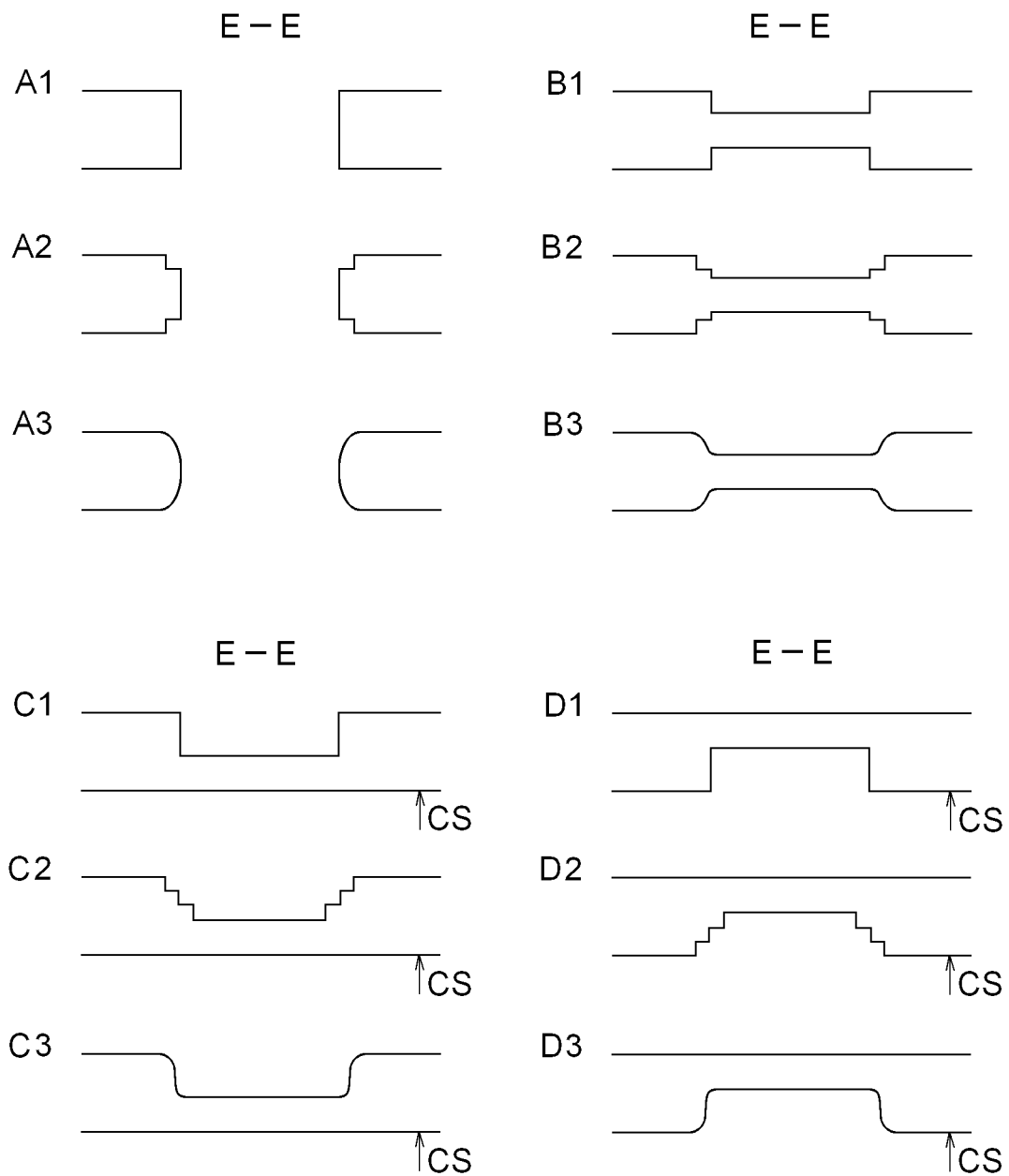
FIG. 3 shows options of openings or recesses in a stent, according to the invention.

FIG. 3 shows options of openings or recessed regions. Openings may have straight (FIG. 3, part A1), stepped (FIG. 3, part A2), curved (FIG. 3, part A3) walls or walls of combined shapes. Recessed regions may have single-stage (FIG. 3, part B1), multi-stage (FIG. 3, part B2), curved (FIG. 3, part B3) transition sites or transition sites of combined shapes. The staged transitions are simpler in production, while curved transitions provide more even distribution of mechanical stress. The recessed regions may be located symmetrically (FIG. 3, part B1, 3, FIG. 3, part B2, FIG. 3, part B3) or asymmetrically (FIG. 3, part C1, FIG. 3, part C2, FIG. 3, part C3, FIG. 3, part D1, FIG. 3, part D2, FIG. 3, part D3) across the strut thickness. Designator "CS" denotes a surface of contact with a vascular wall. Configurations of the recessed regions according to FIG. 3, part C1, FIG. 3, part C2, FIG. 3, part C3 allow maintaining the contact area between a stent and walls of a vessel, and decrease a probability and distance of migration of the stent along the vascular channel, when a radial force exerted by the stent in its expanded state is comparatively low. Configurations of the recessed regions according to FIG. 3, part D1, FIG. 3, part D2, FIG. 3, part D3 provide a higher retaining force owing to roughness of stent contact surface, and decrease probability and distance of migration of the stent along the vascular channel, when a radial force exerted by the stent in its expanded state is comparatively high. The radial force may depend on the stent diameter and some other factors. Therefore, a possibility of choosing a configuration option for openings or recessed regions allows optimizing the stent arrangement, depending on certain conditions of its application.

A stent for treatment in humans may have length from approximately 5 mm to approximately 100 mm, which depends on the vascular disease nature. The minimum value is defined by sizes of atherosclerosis plaques to be treated by intravascular method. Patients suffering from vascular diseases of more than 100 mm long are usually treated using conventional means like bypass surgery or endarterectomy, instead of stent applications. An outer diameter of the stent in its expanded state may be between approximately 0.25 mm and approximately 40 mm. The minimum value depends on a minimum lumen of coronary arteries, while the maximum value depends on a maximum lumen of inferior vena cava and aorta.

Dimensions (width and thickness) of transversal cross-section of struts depend on implantation site of a stent and on required stent mechanical properties. Therefore, there is a need for implementation of streamlined strut shapes; this facilitates avoiding an important component of the Virchow triad (i.e., a set of causes provocative thrombosis), the turbulent bloodstream.

In case of peripheral arteries, an optimal size of struts depends on purpose and place of implantation of the stent. In particular, for renal arteries, thickness of struts may vary from 0.02 mm to 0.5 mm, and width of struts may vary from 0.01 mm to 1 mm. For iliac and carotid arteries having diameter of up to 20 mm, thickness of struts may vary from 0.08 mm to 0.5 mm, and width of struts may vary from 0.08 mm to 1 mm. These parameters are selected so as to avoid turbulent bloodstream through the arteries. When a stent is implanted into coronary arteries, whose diameter may be up to 5 mm, thickness of struts may vary from 0.02 mm to 0.2 mm, and width of struts may vary from 0.02 mm to 0.2 mm Here, thickness of struts means a size of transversal cross-section in radial direction of a stent, and width of struts means a size of transversal cross-section in direction normal to the radial direction.

The above-indicated dimensions of a stent and its structural members are typical for peripheral stents. However, this invention is also applicable to other stent types, e.g., biliary or esophageal stents, as well as for Inferior Vena Cava (IVC) filters. A diameter of biliary stents and dimensions of their struts may be comparable to corresponding dimensions of peripheral stents, but their length may be more than 200 mm. Esophageal stents may have diameter of up to 40 mm and length of up to 250 mm. IVC filters may have diameter of up to 40 mm and length of up to 150 mm.

Stents may be covered with a layer comprising a medical preparation and/or having radiopaque properties. The medical preparation may be, e.g., an antiproliferative agent or an anticoagulative agent. The radiopaque properties may be provided, e.g., using tyrosine-based polymers. The coating also may be a nano-structured coating comprising therapeutic or diagnostic agents, and/or isotopes for providing diagnostics and treatment of oncological and other diseases.

When stents are used for treatment of animals, the stent dimensions may be larger than the above-indicated numbers, and dimensions of stent members may differ from the above-indicated values, depending on vessel sizes of the animals.

Material

A polymer material suitable for manufacturing biodegradable shape memory stents, which mechanical properties at a body temperature of humans and hematothermal animals are sufficient for maintaining a vessel lumen, shall have the following characteristics.

(1) Molecular structure of the material shall include an ester chemical bond or other hydrolyzable chemical bond, which ensures gradual degradation of the material in wet conditions.

(2) The polymer material shall include a single high-molecular compound or a composition of multiple high-molecular and/or oligomeric compounds. The high-molecular compounds may be block copolymers, micro-block copolymers, statistical copolymers, gradient copolymers, star-shaped copolymers, branched copolymers, etc., based on monomer units of one or several types. The monomer units may be represented by cyclic esters (L-lactide, D-lactide, D,L-lactide, meso-lactide, glycolide, ε-caprolactone, trimethylene carbonate, p-dioxanone), as well as by compounds including functional groups capable of photopolymerization like acrylic or fumaric group. A copolymer of a predetermined formulation is obtained by co-polymerization of monomer units or oligomers based on monomer units, or by chemical bonding pre-synthesized oligomeric or polymeric crystallite structures. The copolymer having a molecular weight of 20 kDa to 600 kDa, preferably 100 kDa to 400 kDa, may be represented by a poly(L,L-lactide-co-ε-caprolactone), poly(L,L-lactide-co-trimethylene carbonate), poly(glycolide-co-ε-caprolactone) and other copolymers in a ratio of approximately 100:1 to approximately 1:100. A composition based on multiple materials may be obtained by mixing in an extruder. Such a composition may be represented by, e.g., a mixture of poly(L,L-lactide) and poly(D,D-lactide-co-ε-caprolactone), where poly(L,L-lactide) chains and poly(D,D-lactide-co-ε-caprolactone) chain segments represented by D,D-lactide monomer units jointly form a stereocomplex having an increased melting temperature and improved physical and mechanical properties.

(3) The material shall have main glass transition temperature and main melting temperature of above 37 degrees Celsius to provide mechanical properties of an article during its operation inside a human's body to be sufficient for maintaining a vessel lumen.

(4) The molecular structure of the material shall be stereoregular or be able to form cross-links so as to ensure a possibility of crystallization of the material during annealing, or be able to constitute a molecular network for formation of a permanent shape of the stent.

(5) The molecular structure of the polymer material shall include an additional polymeric or oligomeric component that undergoes a relaxation and/or phase transition upon heating to 30-37 degrees Celsius and/or in wet conditions and/or under exposing to another predetermined external effect, which transition is accompanied by change from temporary shape to permanent shape of a stent.

(6) Formation of the temporary shape of a stent is performed by heating the stent over its supplementary component glass transition or melting temperature, but still below its main component glass transition or melting temperature, and by sharp deformation to a required temporary shape. If the supplementary or oligomeric component is represented by amorphous phase, the stent is fast quenched at minus 20 degrees Celsius or a lower temperature right after the deformation. If component is represented by crystallizable polymeric or oligomeric chains, then annealing is performed at a crystallization temperature to fix the temporary shape.

(7) A predetermined permanent shape of a stent may be changed by deforming the stent to a new permanent shape and annealing the newly deformed stent at a temperature above the main glass transition temperature, but below the main melting temperature.

As discussed above, the copolymer molecular weight may be 20 kDa to 600 kDa, preferably 100 kDa to 400 kDa. The lower limit of the molecular weight is defined by requirement of maintaining mechanical properties of the stent for at least one month after implantation thereof. The upper limit is defined by a high viscosity of the material melt and technological problems related to extruding a stent workpiece. Another factor that limits the upper limit of the molecular weight is excessively slow decomposition of the high-molecular polymer (molecular weight of the stent material gradually decreases during operation of a stent due to its biological degradation inside an organism).

Polydispersity index (PDI) of the copolymer shall be 1.3-2.5, preferably 1.5-2.0. The range of acceptable values of polydispersity index shall be narrow enough so as to provide controlled stent degradation. If the PDI value is above 2.5, oligomeric fractions in the material may cause self-excited acceleration of degradation due to a high concentration of acidic groups. This, in turn, may lead to early loss of mechanical properties of an article. The lower limit of the PDI value relates to technological restrictions for the above-indicated materials, in particular, a PDI value of less than 1.3 is hard to obtain in practice.

The above-discussed theoretical basis and real-life experiments described below give the inventors grounds to state that the objects of the stent are achieved and its claimed characteristics are ensured in the entire range of the above-indicated polymer molecular weight and polydispersity index values.

The main component glass transition temperature shall be not lower than 37 degrees Celsius. With a lower glass transition temperature, a stent would have to operate inside an organism under conditions above the glass transition temperature, which would cause a critical decrease in its mechanical properties. Preferably, the main component glass transition temperature shall be not lower than 42 degrees Celsius to ensure the required mechanical properties of a stent, when body temperature is elevated due to an intensive immune response of an organism.

Figure 4:
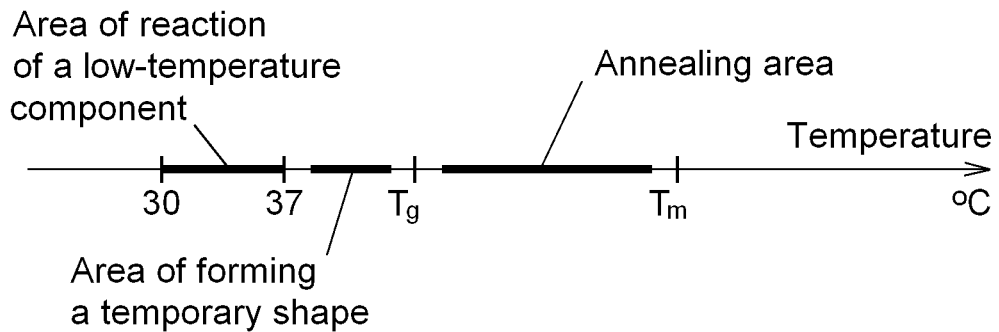
FIG. 4 shows locations of representative production process points and areas in temperature domain; $T_g$ is a glass transition temperature, $T_m$ is a melting temperature.

FIG. 4 shows locations of representative production process points and areas in temperature domain.

A modulus of elasticity of the material shall be at least 400 MPa at 37 degrees Celsius. Ultimate rupture strength value shall be at least 10 MPa at 37 degrees Celsius. If the above parameters are lower, mechanical properties of a stent would not be acceptable, i.e., the stent would not be able to maintain a required vascular lumen.

Melting enthalpy of annealed material (for crystallizable materials) shall be at least 20 J/g. Crystallinity degree is closely related to melting enthalpy. In order to provide required mechanical properties of a stent during its operation inside an organism, it shall have a semi-crystalline structure. As a stent shall be functional at a temperature just slightly lower that glass transition temperature of its material, the material amorphous component is in a highly elastic state, so the modulus of elasticity of the material may be non-sufficient to perform support function, when the crystallinity degree is not high enough.

Manufacturing Technology

A stent production process consists of a number of technological steps. Steps of a production process for a stent having outer diameter of 10 mm in expanded state (i.e., the permanent shape) and 2.5 mm in reduced state (i.e., the temporary shape) are described further as an example.

Step 1: drying the material. Pellets of a polymer material are fed in as an input. The pellets are dried in a vacuum chamber at temperature of 70 degrees Celsius for approximately three hours at pressure of 0.1 MPa. As an output, dehydrated pellets are obtained. The dehydration is used to minimize destruction of the material during its processing in an extruder and, correspondingly, to ensure the above-indicated chemical and physical characteristics of the material.

Step 2: extrusion. Dried pellets are fed in as an input. The pellets are loaded into an extruder having a die for producing a tube. With no additional processing, the tube material at the die output will be amorphous. To obtain a semi-crystalline tube, annealing is performed, i.e., the tube is kept at a temperature of above 100 degrees Celsius for 15-60 minutes. The annealing step may be done in a continuous mode, e.g., by passing the tube through a long heater, or in discontinuous mode, e.g., by loading a batch of extruded tube into a heater. The use of dies having a special configuration is also possible, where the dies are capable of properly directing crystallite structures of the material during crystallization of the tube material to provide a specifically oriented crystallite (i.e. supramolecular) structure. The higher crystallinity degree of the stent material, the better its mechanical properties shall be after recovery of the stent initial shape. As an output, a partially crystalline tube of required diameter is obtained.

Extrusion of the tube may be performed instead by spraying or sputtering a material onto a cylindrical base, followed by removing the formed tube from the base. Alternatively, a tube may be obtained by immersing a base into a material melt with subsequent curing. Comparatively large stents may be obtained by hot pressing, molding in automatic injection machines, or by deposition a special mixture in rotational machines. In some cases, a tube may be formed by blow-stretching at a temperature higher that the main glass transition temperature, but lower than the main melting temperature.

Figure 5:
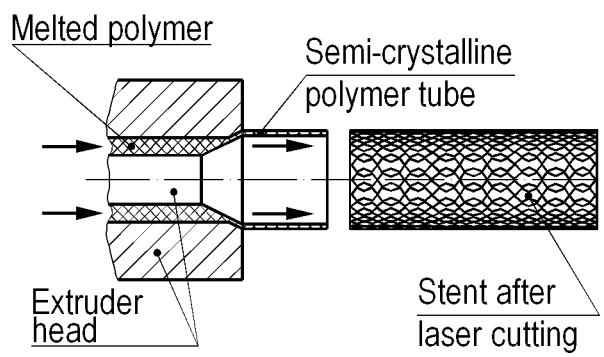
FIG. 5 shows a generalized process flow providing a longitudinal/radial orientation of tube material crystallite structures according to [21].

Usual (static) extrusion heads provide longitudinal orientation of the tube material supramolecular structure, according to their operating principle. In [21] a combined longitudinal-radial orientation of crystallite structures (at an angle of about 30° relative to the longitudinal axis of the tube) is proposed to be provided by a die having a divergent taper configuration. FIG. 5 shows a generalized diagram of the method according to [21]. In the opinion of the inventors, this solution cannot sufficiently improve stent mechanical properties at the place of its application.

Figure 6:
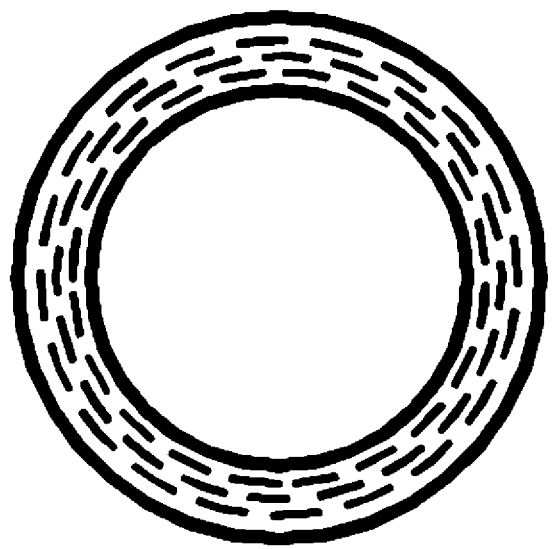
FIG. 6 shows substantially circular orientation of tube material crystallite structures, when seen in transversal cross-section of the tube.

In order to ensure improved stent mechanical properties, this invention provides a different orientation of the tube material supramolecular structure. In an illustrative embodiment of the invention, a spiral orientation of crystallite structures is provided by rotational movement of an extrusion head during extrusion process. With a sufficiently large ratio between number of revolutions of the extrusion head and longitudinal extrusion rate, a small pitch spiral may be obtained, i.e., orientation of the tube material supramolecular structure may be substantially circular, when seen in transversal cross-section of the tube, as shown in FIG. 6. This kind of supramolecular structure allows greatly increasing a radial force generated by the stent during its deployment and a radial load that the stent is able to resist during its operation with no any noticeable narrowing lumen of the vessel where the stent is deployed, compared to stents having longitudinal or longitudinal-radial orientation of crystallite structures known in the art.

Step 3: laser cutting. A partially crystalline tube of a required diameter, e.g., 10 mm, is fed as an input. The tube is subject to laser carving to obtain a lace-like wall with cells of closed type, e.g., as shown in FIG. 1, and further it is cut into pieces of required lengths. Afterwards, the stent is washed in water and/or alcohol, and/or other appropriate solvent to remove process contaminations and material offcuts from the stent surface, and is dried, e.g., in a vacuum cabinet. As an output of the step, a stent of substantially the same diameter is obtained, which diameter corresponds to the permanent shape of the stent, to which the stent will return owing to shape memory effect, when heated to approximately 37 degrees Celsius.

Step 4: crimping; Step 5: sterilization; Step 6: packing; Step 7: marking. A stent of a required diameter, e.g., 10 mm, is fed as an input. The stent is placed into a fixture providing uniform crimping over entire outer surface (so called "diaphragm jaws"). Crimping is performed by heating the stent to 50-60 degrees Celsius and sharply crimping it to a diameter corresponding to a delivery means diameter. After crimping, the reduced stent is immediately inserted into a delivery device (a catheter), further it is quenched at temperature of approximately minus 20 degrees Celsius or lower, and sterilized, e.g., using radiation (gamma or beta radiation) or chemical (ethylene oxide) or plasma (low-temperature plasma $H_2O_2$) sterilization method. Afterwards, the stent is hermetically packed, marked and placed into a freezer, where a temperature of approximately minus 20 degrees Celsius is maintained.

It is important to provide a fast (not more than 30 seconds) chilling the stent after crimping; otherwise relaxation of polymer chains during a slower chilling may result in substantial deterioration of shape memory effect and, correspondingly, in decreasing allowable radial load of the stent during its operation.

Application Method

Preoperative preparation. Prior to surgery, non-invasive methods of examination shall be used to determine stenosis degree, e.g., color duplex ultrasonography of brachiocephalic arteries and/or spiral computer tomography in angiographic mode. It is important to obtain information on condition of all extracranial vessels (aortic arch branches) and Willis artery ring. Additionally, it is necessary to conduct a thorough neurological examination as well as cerebrum computer tomography and/or cerebrum magnetic resonance imaging so that the change history after the stent deployment may be assessed. Additionally, organs and systems shall be examined in patients suffering from severe concomitant diseases (electrocardiogram, echocardiogram, doctor's advice, etc.). It may be advisable to administer antiplatelet agents (e.g., Clopidogrel 75 mg per day) for two or three days prior to the stent deployment.

Operative methodology. The implantation operation is performed under local anesthesia with intravenous sedation. This approach allows monitoring neurological status during the deployment operation. In order to control a linear bloodstream rate along the medial cerebral artery and to control passage of micro-emboli, the deployment operation must be performed with dopplerographic monitoring. A final estimation regarding stenosis degree may be done after acquisition of angiographic data.

Mostly, a transfemoral access is used; if reasons preventing that assess are discovered, another access (via a radial artery or an axillary artery) may be used. Immediately after puncture of artery, 5000 units of Heparine shall be administered; further, Heparine is administered iteratively each 40-60 minutes, and activated clotting time is monitored. Selective angiography of aortic arch branches allows detecting multifocal lesions of iliac arteries and selecting (or changing) therapeutic approach.

Stenting. In some cases, a preparatory dilation of artery (i.e., inflating a balloon in the stenosis site prior to stent implantation) may be needed. This is applicable when a vessel is so narrowed that insertion of a stent delivery system is not possible.

The next phase is stent delivery and implantation. Stents are technically not deformable and they exert a constant pressure on a vessel wall after implantation. A stent is positioned so that its distal and proximal portions overlap the stenosis site by at least 5 mm A control angiography shall be conducted immediately after implantation to assess degree of residual stenosis. In most cases, radial force provided by the stent of the invention is enough to ensure a required vessel lumen. Additional dilation (inflating a balloon inside the implanted stent) may be applicable if the residual stenosis degree is more than 30%. When the stenting operation is over, a trap filter is removed using a special tool, when applicable. After the filter removal, a control angiography shall be conducted again.

Verification of Attaining the Technical Result

Figure 7:
FIG. 7 shows a model of a ring member of an endovascular stent, according to the invention.

Theoretical estimations with computer simulation and real-life experiments were performed by the inventors to verify possibility of attaining technical result. Crimping simulation and estimation of stent mechanical properties FIG. 7 shows a model of a ring element of endovascular stent, having the following geometric characteristics: thickness of struts is 400 μm, width of struts is 350 μm, length of the element is 10.7 mm, inner diameter is 10 mm, cell pattern is of the type shown in FIG. 1.

It should be noted that stent length is not limited by the ring element length. A stent may consist of multiple ring elements, which constitute a whole integral article. Preferably, stent lengthwise cutting is performed in multiples of the ring element length; however, the stent may be cut off in any place, if needed.

Figure 8:
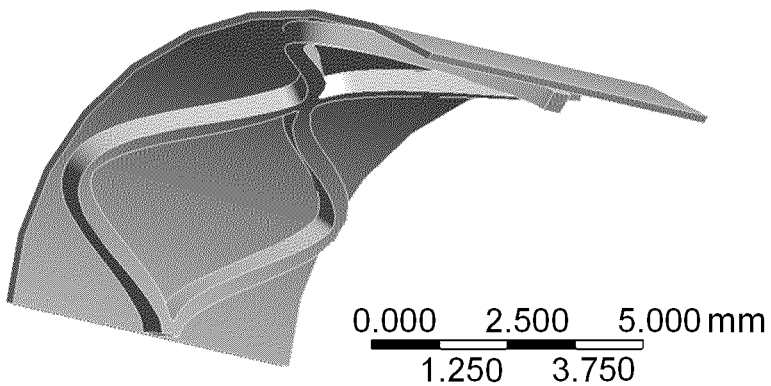
FIG. 8 shows a segment of a model of a ring member of an endovascular stent according to the invention, which was used in the calculations.

In order to reduce computational load, a segment of the ring element and a corresponding crimper segment of 120° were used for numerical solution of the simulation task, as shown in FIG. 8. The simulation was done using ANSYS software tool that is based on finite element method. A Mesh Independence Test was performed to determine an optimal finite element size. As a result, the stent finite element size was selected to be 0.07 mm and the crimper finite element size was selected to be 0.1 mm.

Figure 9:
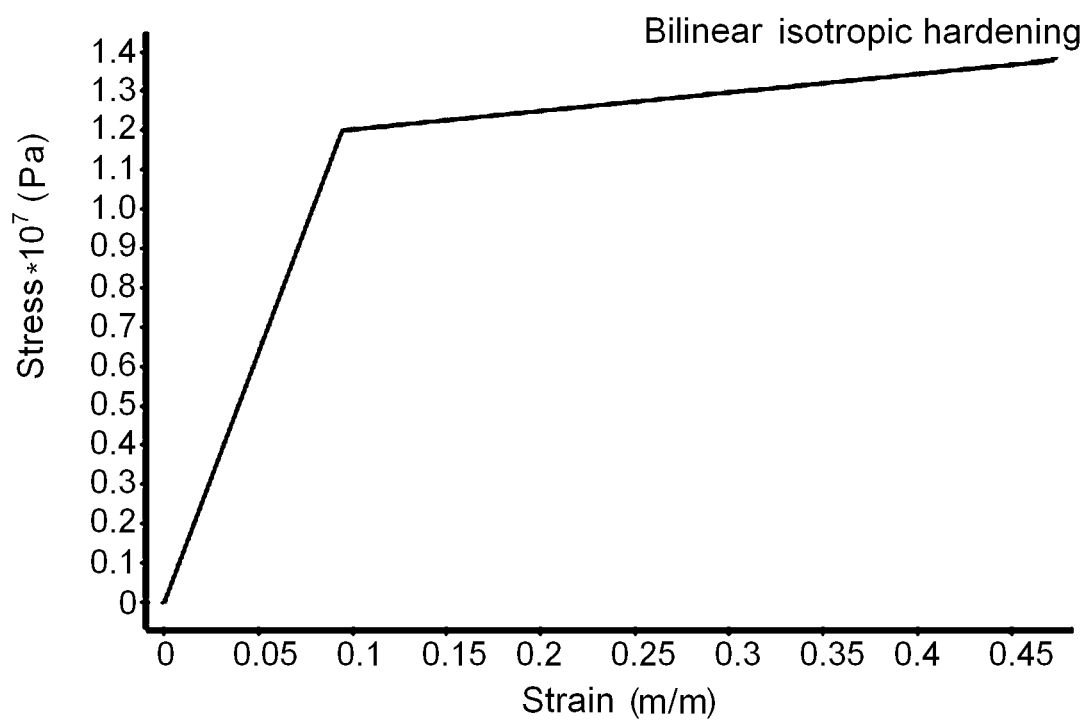
FIG. 9 shows a diagram corresponding to a finite-element model of a stent material according to the invention, which was derived from a diagram of a one-axis tension represented in FIG. 10.
Figure 10:
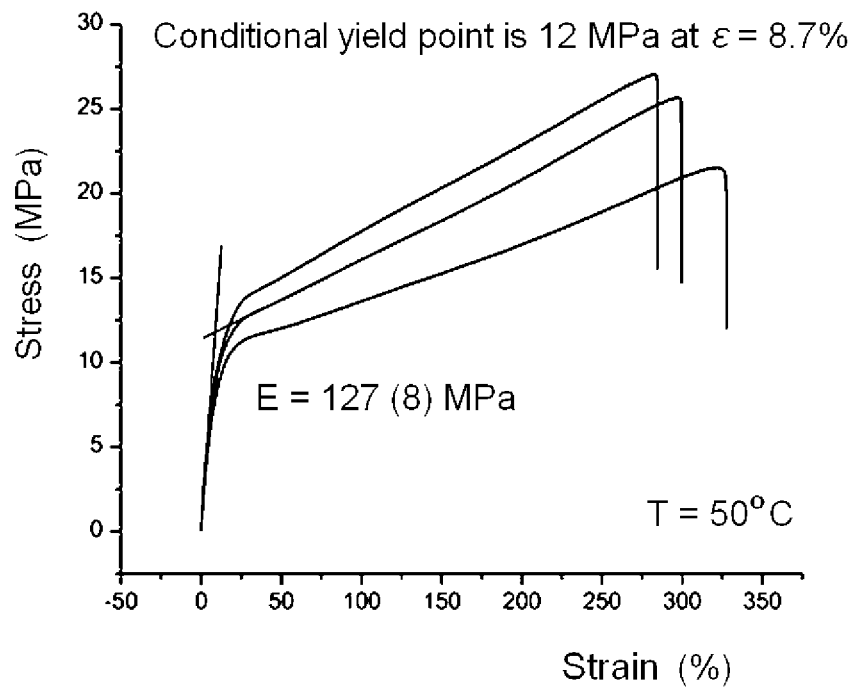
FIG. 10 shows a diagram of a one-axis tension, based on which the finite-element model of a stent material of FIG. 9 was derived.

Simulation of preliminary stent crimping was done by radial moving the outer surface of the crimper. Boundary conditions were applied to edges, taking into account the model symmetry. An additional restriction related to circular movement was applied to the outer surface of the stent to exclude moving the stent as an integral rigid body. Finite element model of the stent material (FIG. 9) derived from one-axis strain diagram at 50 degrees Celsius (FIG. 10) was employed for calculations. Convergence of the solution was verified by force and movement criteria. A Large Deformation Function was used for description of considerable movements of the elements.

Figure 11:
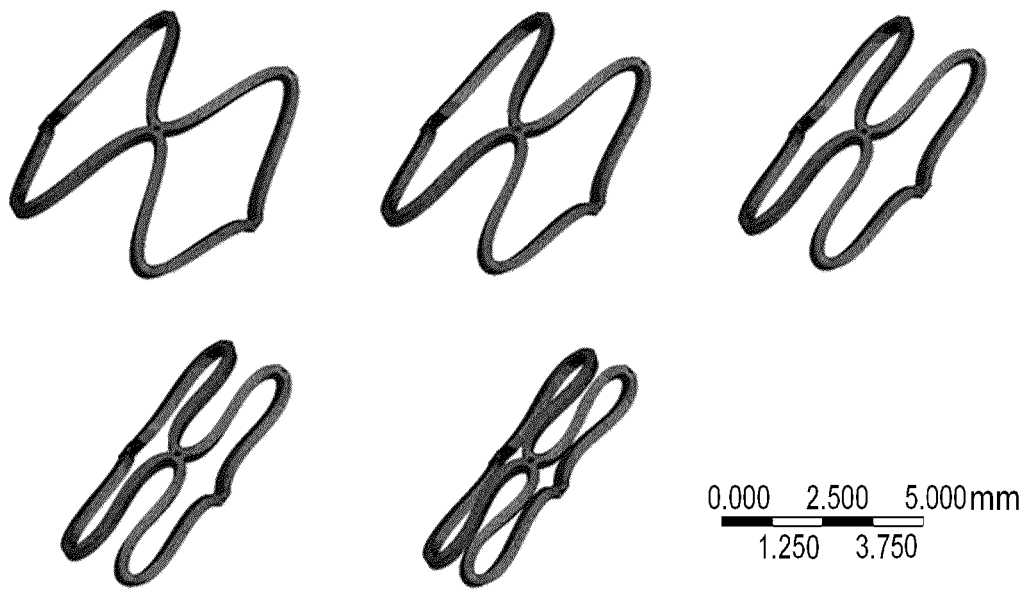
FIG. 11 shows phases of a crimping process for a stent according to the invention, where initial inner diameter is 10 mm, and final inner diameter is 2.5 mm.

FIG. 11 shows phases of crimping process for a stent having initial inner diameter of 10 mm and final inner diameter of 2.5 mm. Analysis of mechanical stress occurring in the stent during crimping with the above-indicated parameters has shown that dependence of the stress value remains linear up to a reduction of the inner diameter by using crimping by 3.75 mm on each side, which corresponds to a final stent inner diameter of 10−2×3.75=2.5 mm. Deformations do not exceed acceptable values during the reduction, which assures absence of cracks in the stent material. Further reduction is impeded by contact between struts and it may lead to destruction of the stent during production or to excessively fast degradation of the stent inside an organism. However, analysis done by the inventors has shown that the allowable inner diameter value may be decreased to 2.0 mm by improvement of the strut shape.

Simulation Summary

In order to enable crimping a stent onto a delivery device having an outer diameter of 2 mm, it is necessary to decrease the cell length. This would allow increasing radial rigidity of the arrangement and ensuring tough engagement of lamellas to the delivery device surface. Analysis of stress-strain conditions in the stent arrangement shows that stress and deformations do not exceed critical values, which exclude formation of cracks in potentially risky areas. High plasticity of the material at 50 degrees Celsius allows deforming the stent with no excessive forces emerging in the stent, which would lead to its destruction or to deteriorating its operational parameters. Radial forces values (at least 0.05 N with inner diameter of 2.5 mm) are caused by mechanical properties of the material at 50 degrees Celsius and peculiar deformation-related behavior of the stent.

Generally, the simulation has shown that 5× change in the stent diameter during crimping should not be accompanied by emerging cracks and other defects in the stent material. Actual stent reduction degree depends on a number of factors, in particular, on the initial stent diameter. For example, in case of stent small diameters (for very small vessels), change in stent diameter may be 3× to 4×, depending on type and characteristics of the stent delivery system.

Experimental Study

Molecular weight characteristics of the polymer were determined by Gel Permeation Chromatography using a Knauer analytical chromatograph equipped with a degasser, a pump, a thermostat and a refractometric detector. A sample was dissolved in tetrahydrofuran of "HPLC-grade" purity and injected into a chromatographic system. Tetrahydrofuran of "HPLC-grade" purity was used as an eluent at flow rate of 1 ml per minute. An Agilent PLgel column having pore size of $10^5$ Å and particle size of 5 μm was thermostabilized at 40 degrees Celsius and its calibration was performed using polystyrene standards.

Chemical composition of the material was studied by $^1$H-Nuclear Magnetic Resonance (NMR) method. A sample was dissolved in deuterated chloroform. Chemical composition of the polymer material was calculated, based on integral intensity of signals in an NMR spectrum. Physical/mechanical properties of the material were studied using an Instron test machine.

Figure 12:
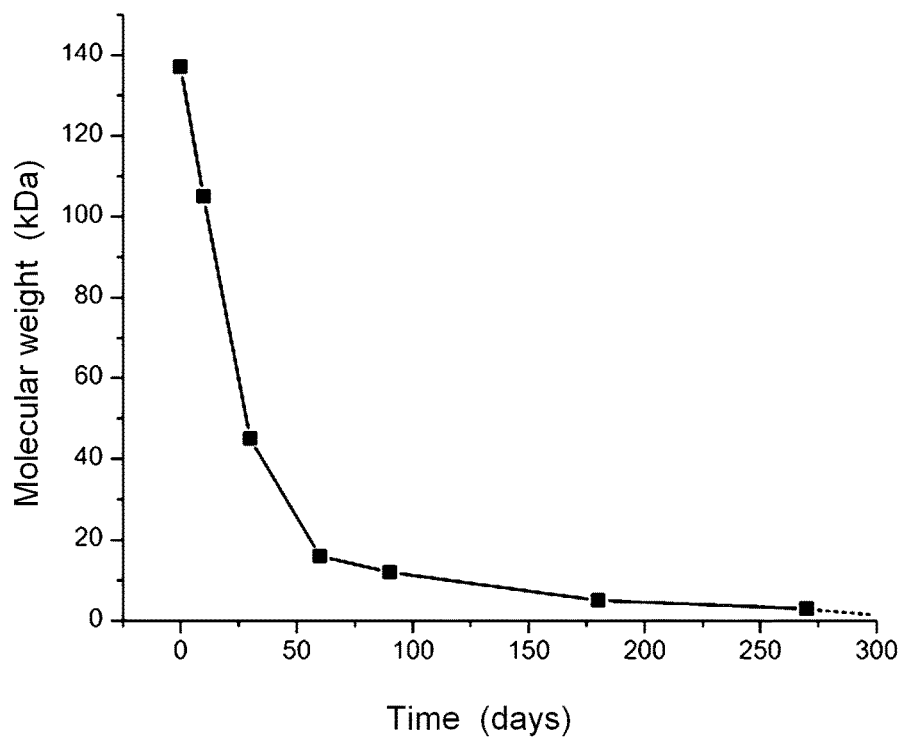
FIG. 12 shows a diagram of degradation of a polymer used in a stent according to the invention, in a phosphate buffer at 37 degrees Celsius.

Polymer degradation was studied in phosphate buffer at 37 degrees Celsius using rectangular plate samples having dimensions of 55×10×1 mm of L-lactide and ε-caprolactone copolymer having initial molecular weight of approximately 140 kDa. Experimental results are shown in FIG. 12. It is apparent from the figure that molecular weight sharply decayed for the first 50 days from the initial value to approximately 20 kDa, and after that, the decay rate was clearly decelerated. Generally, the degradation dependence on time was about exponential.

Figure 13:
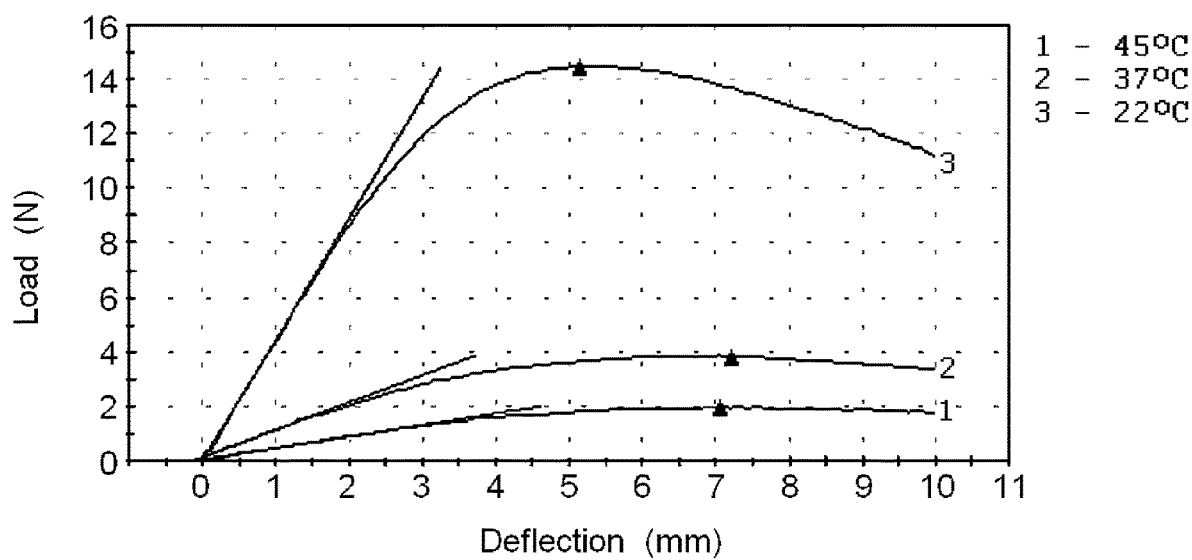
FIG. 13 shows deformation curves of plate samples at different temperatures, the samples made of a polymer used in a stent according to the invention.

Rectangular plates having dimensions of 55×10×1 mm made of L-lactide and ε-caprolactone copolymer were used for studying polymer mechanical properties at deflection of 10 mm Experimental results represented in FIG. 13 (stress-strain curves at different temperatures) and in FIG. 14 (values of modulus of elasticity) show that the load value causing deflection of 10 mm at 37 degrees Celsius is substantially lower than the corresponding load value at 22 degrees Celsius and somewhat higher than the corresponding load value at 45 degrees Celsius. The modulus of elasticity drops from approximately 2985 MPa at 22 degrees Celsius to approximately 664 MPa at 37 degrees Celsius and further decreases to approximately 281 MPa at 45 degrees Celsius.

Similar samples were used for studying shame memory effect. A sample was placed into a test chamber preheated to 45 degrees Celsius and kept for 5 minutes. Further, the sample was deformed with a rate of 100 mm per minute to form deflection of 10 mm (FIGS. 16A, 16B), then it was quenched in liquid nitrogen and removed from the chamber.

After that, the sample was placed in a room temperature environment and temporal change in residual deformation was observed. FIG. 15, part C shows the sample immediately after chilling (its length is approximately 45 mm); FIG. 15, part D shows the sample in 1.5 hours (its length is approximately 50 mm). This result indicates a rather stable shape of the deformed sample at a room temperature (approximately 22 degrees Celsius).

Further, temporal change in mechanical properties of a sample was studied during temperature increase up to 37 degrees Celsius. To do that, the sample, after holding at a room temperature, was placed into a test chamber having 22 degrees Celsius temperature inside and a load of approximately 0.2 N was exerted upon a central portion of the sample, as shown in FIG. 15, part B. Then the chamber was set to heating to 37 degrees Celsius and change in the sample recovery force was measured while maintaining constant deformation. The measurement results are shown in FIG. 16. It shows that during the chamber heating at rate of 15 degrees Celsius per minute, the recovery force increased fast between 0 and $1^{st}$ minute owing to shape memory effect, then a transitional process with slowed increase of the recovery force was observed between $1^{st}$ and $4^{th}$ minute, afterwards the recovery force was almost constant under substantially isothermal conditions (approximately 37 degrees Celsius) between $4^{th}$ and $10^{th}$ minute.

Further, mechanical properties of a sample were studied during temperature increase up to 40 degrees Celsius. With a temperature rise from 22 to 40 degrees Celsius, the recovery force increased monotonically in temperature range of approximately 30 to approximately 40 degrees Celsius (FIG. 17). The column height in the diagram represents change in load within one degree. This test was performed twice with different samples and their results were quite similar, as it can be seen in the diagram of FIG. 17.

After unloading and holding at temperature of 37 degrees Celsius for three minutes, almost full recovery to the initial shape of the sample was observed (FIG. 15, part E).

Experiment Summary

A. With decreasing material molecular weight to 1 kDa or less, the material becomes soluble in water and is metabolized by an organism via Krebs cycle. A period of total resorption of the copolymer is estimated to be 300 days. A period of maintaining mechanical strength inside an organism is estimated to be 2-3 months.

B. Maximum sample tension during the inflection test was 17.5 MPa and maximum elasticity modulus value was 664 MPa, which suggests acceptable mechanical properties of a stent produced in accordance with the inventive technology.

C. Copolymer samples are able to maintain a temporary (bent) shape at room temperature and respond to heating. Shape recovery starts at approximately 31 degrees Celsius. Force generated during that technically does not recede after holding for 10 minutes at temperature of 37 degrees Celsius.

Implementation Examples

A peripheral cylinder stent was produced to validate the above-discussed concepts. The stent had length of 53 mm, outer diameter of 10 mm (in expanded state) and a pattern of struts as shown in FIG. 1.

The material composition was controlled by the above-described method, which results were as follows: material was poly(L,L-lactide-co-ε-caprolactone) with molar ratio of L,L-lactide 68,5%, ε-caprolactone 31,5%; average molecular weight was 200 kDa or more; polydispersity index was 2.0. The material was dried at 70 degrees Celsius for three hours in a vacuum cabinet.

The material was loaded into a Haake Minilab extruder equipped with an appropriate die and an amorphous tube having outer diameter of 10 mm was obtained at 200 degrees Celsius, according to the instructions by the extruder manufacturer. Annealing was performed at temperature of 110 degrees Celsius and pressure of 0.1 MPa for 20 minutes to obtain a partially crystalline tube.

The partially crystalline tube was laser carved according to the above-described option of the lace pattern, and further it was cut to pieces 53 mm long so as to obtain separate stents. After cutting, the stents were washed in water and ethanol to remove possible contaminations and dried in a vacuum cabinet at 40 degrees Celsius for 20 minutes.

Each stent was further placed into a crimping fixture of "diaphragm jaws" type to compress the stent into a temporary (reduced) shape and to pack the stent into a catheter. Crimping was performed by way of heating the stent to 50 degrees Celsius and sharply crimping to outer diameter of 2 mm After crimping, the reduced stent was immediately inserted into a delivery device (a catheter), then it was fast quenched at minus 20 degrees Celsius, packed and hermetically sealed. After packing, sterilization was performed by gamma-radiation with exposure of 25 kGr. Afterwards, the stent was placed into a freezer and further stored in temperature range of minus 20 to minus 25 degrees Celsius until application.

Measurements of the prototype series stents yielded the following results:
  outer diameter in reduced state was 2.1±0.1 mm;
  outer diameter in expanded state was 9.8±0.5 mm;
  width of struts was 350±50 μm;
  thickness of struts was 400±5 μm;
  time of stent expanding to 80% of initial diameter at 37 degrees Celsius was 3 minutes;
  time of total stent expanding at 37 degrees Celsius was 15 minutes;
  elasticity modulus at 37 degrees Celsius was at least 540 MPa;
  period of maintaining at least 70% of initial stent mechanical properties was 80 days;
  period of total stent resorption was 300 to 500 days.

FIG. 18 shows a flattened view of another option of the stent wall strut pattern. Like in the option of FIG. 1, the stent wall is also formed by a closed-cell structure, but of another configuration. In this option, cell has a more complex shape, which is enlarged in FIG. 19. The cell prior to crimping may be represented by a set of struts connected to each other so as to form angles α, β, γ. The struts may have fillets having radii $R_1$-$R_9$, as shown in FIG. 20.

This cell arrangement allows decreasing stress occurring in the struts during crimping, and at the same time reducing turbulence of the blood flow with no deterioration of radial rigidity of the stent in its expanded state. Cells of this type allow ensuring a balance between high radial rigidity, resilience and flexibility of the stent.

The width of struts may be 0.01 to 1 mm and thickness of struts may be 0.02 to 0.5 mm, depending on the stent diameter. Characteristic angle α relates to angles β and γ by the following ratio $$\frac{\alpha}{2} + \beta - \frac{\gamma}{2} = 90°$$

and its value depends on stent diameter and width of struts. In the example of FIG. 20, values of these angles are: α=γ=110°, β=90°. Fillet radii $R_1$-$R_9$ may be 0.025 to 1 mm Values of these radii in certain embodiments of the invention depend on geometric dimensions of the stent members, in particular, the width of struts. For example, $R_2$=$R_1$+W, where W is width of struts at the rounding place; the $R_1$ value also correlates with the W value. Values of radii $R_1$, $R_3$, $R_4$, $R_5$, $R_7$ and $R_9$, as well as $R_2$ and $R_8$ may be substantially equal to each other or similar enough to within several percent (or within a manufacturing tolerance).

FIGS. 19-21 show struts having strait portions between the rounding places. However, these portions may be curved or constitute a combination of straight and curved portions.

Like in the option of FIG. 1, the width of the struts shown in FIG. 19 may be increased in places of maximum mechanical stress that occurs during production or during operation of the stent. Struts may also have decreased thickness and/or openings in places of minimum mechanical stress that occurs during production or during operation of the stent.

Prototype samples with strut pattern shown in FIG. 18 were tested. Technology of manufacturing these samples was substantially the same as described in the above.

Sample 1U: outer diameter prior to deformation was 10.0 mm; outer diameter after deformation was 7.6 mm; length prior to deformation was 20.2 mm; length after deformation was 25.0 mm; number of cells was 5, width of struts was 0.2 mm; stent material was annealed. The sample was circularly reduced to outer diameter of 2.3 mm at 36.6 degrees Celsius with a deformation rate of 1 mm per minute, held with this load for 10 seconds and then unloaded at the same rate.

Sample 2U: outer diameter prior to deformation was 10.2 mm; outer diameter after deformation was 7.7 mm; length prior to deformation was 20.4 mm; length after deformation was 25.4 mm; number of cells was 5, width of struts was 0.2 mm; stent material was annealed. The sample was circularly reduced to outer diameter of 2.3 mm at 36.6 degrees Celsius with a deformation rate of 1 mm per minute, held with this load for 10 seconds and then unloaded with the same rate.

Sample 3U: outer diameter prior to deformation was 10.0 mm; outer diameter after deformation was 6.0 mm; length prior to deformation was 22.5 mm; length after deformation was 26.2 mm; number of cells was 5, width of struts was 0.2 mm; stent material was not annealed. The sample was circularly reduced to outer diameter of 2.3 mm at 36.6 degrees Celsius with a deformation rate of 1 mm per minute, held with this load for 10 seconds and then unloaded with the same rate.

Sample 4U: a stent similar to the sample 2U was crimped: it was preheated for 10 minutes at 50 degrees Celsius, reduced with deformation rate of 1000 mm per minute (maximum allowed equipment rate) and quenched in liquid nitrogen for 10 minutes. Prior to testing, the stent was allowed to expand and held at 36.6 degrees Celsius until its shape became stable. Outer diameter prior to deformation was 8.5 mm; outer diameter after deformation was 8.2 mm; length prior to deformation was 24.2 mm; length after deformation was 24.5 mm; number of cells was 5, width of struts was 0.2 mm; stent material was annealed. The sample was circularly reduced to outer diameter of 2.3 mm at 36.6 degrees Celsius with a deformation rate of 1 mm per minute, held with this load for 10 seconds and then unloaded with the same rate.

FIG. 21 shows a diagram representing specific radial force depending on outer stent diameter for stents having the strut pattern according to FIG. 1 and according to FIG. 18. The same dependence is also shown for a best-of-breed metal scaffold named Niti Stent Cordis (Smart), which had diameter of 5.0 mm and length of 35.0 mm in its initial state. It should be noted that the polymer stent according to the invention after crimping (Sample 4U) possesses characteristics comparable to characteristics of the metal stent (Cordis) in the middle range of diameter values (4.2-4.6 mm); moreover, its characteristics are suffitiently better for larger diameter values (4.6-5.0 mm).

FIG. 22 shows substantially the same experimental data as FIG. 21, but in a more representative form. In particular, FIG. 22 shows a diagram representing specific radial force depending on ratio of actual outer diameter after deployment and nominal outer diameter of the stents under test, Sample 4U and the above-mentioned CORDIS scaffold. The diagram clearly shows that the polymer stent according to the invention after crimping (Sample 4U) has generally the same or better operational properties, compared to the reference scaffold, when its outer diameter after deployment is in a range of 100% to about 87% of its initial diameter before crimping and has somewhat less but still acceptable properties in a range of about 87% to about 80% of its initial diameter.

The above-indicated experimental results show that mechanical properties of the stent according to the invention may be further improved by refinement of the stent wall closed-cell pattern. This also proves possibility of attaining the claimed technical result.

Thus, the technology according to the invention allows providing biodegradable polymer stents for peripheral, coronary, cerebral arteries and veins, bifurcated scaffolds, stent-grafts, biliary stents, esophageal stents, as well as IVC filters.

Possible Improvements of the Invention

Further improvement of the inventive stent characteristics may be achieved by optimization of molecular and supramolecular material structure, which may allow accelerated expansion of the stent in application site and increasing its load-carry capability. Moreover, using coatings to decrease degradation rate of the stent material during initial weeks after deployment in situ is also possible. For example, hydrophobic coatings may be used to limit contact between the stent material and water. Such coatings allow step-shaping the polymer degradation curve (FIG. 12) to provide an initial flat portion of the curve.

It should be noted that the sequence of actions described in the illustrative embodiment of the invention may be different in another embodiments. For example, sterilization of a finished stent may be done prior to packing or after packing, depending on the used sterilization method. Cutting the stent workpiece into separate pieces may be done prior to laser carving, or after laser carving but prior to crimping, or after crimping, depending on the stent dimensions and/or technological capabilities of the manufacturer. Thus, the sequence of actions recited in the method description is merely illustrative and it may differ from what is described, if the function is maintained and the result is achieved in various embodiments.

It should also be noted that the above description recites those steps only, which are the most essential for achieving the invention purpose. It should be apparent to a person skilled in the art that additional steps shall be performed to obtain a desirable result, the steps defined by the production and/or application technology of the stent according to the invention.

Parts and features of the invention may be combined in different embodiments of the invention to an extent so as they do not contradict to each other. The embodiments of the invention described in the above are provided as illustrations and they are not intended to limit the invention, which is defined in claims. All and any reasonable modifications, alterations, and equivalent replacements in design, configuration, and principle of operation within the invention gist are included into the invention scope.

REFERENCES (ALL INCORPORATED HEREIN BY REFERENCE IN THEIR ENTIRETY)

1. Liang Xue, Shiyao Dai, Zhi Li. Biodegradable shape-memory block co-polymers for fast self-expandable stents. DOI: 10.1016/j.biomaterials.2010.07.043
2. Koji Nagahama, Yuichi Ueda, Tatsuro Ouchi, Yuichi Ohya. Biodegradable Shape-Memory Polymers Exhibiting Sharp Thermal Transitions and Controlled Drug Release. DOI: 10.1021/bm9002078
3. Christopher Michael Yakacki, Robin Shandas, Craig Lanning, Bryan Rech, Alex Eckstein, Ken Gall. Unconstrained recovery characterization of shape-memory polymer networks for cardiovascular applications. DOI: 10.1016/j.biomaterials.2007.01.030
4. Debdatta Ratna, J. Karger-Kocsis. Recent advances in shape memory polymers and composites: a review. DOI: 10.1007/s10853.007.2176.7
5. Maria Balk, Marc Behl, Christian Wischke, Jörg Zotzmann, Andreas Lendlein. Recent advances in degradable lactide-based shape-memory polymers. DOI: 10.1016/j.addr.2016.05.012
6. Subbu S Venkatraman, Lay Poh Tan, Joe Ferry D Joso, Yin Chiang Freddy Boey, Xintong Wang. Biodegradable stents with elastic memory. DOI: 10.1016/j.biomaterials.2005.09.002
7. Andreas Lendlein, Jörg Zotzmann, Yakai Feng, Armin Alteheld, Steffen Kelch. Controlling the switching temperature of biodegradable, amorphous, shape-memory poly(rac-lactide)urethane networks by incorporation of different comonomers. DOI: 10.1021/bm900038e
8. Peng Ping, Wenshou Wang, Xuesi Chen, Xiabin Jing. Poly(ε-caprolactone) polyurethane and its shape-memory property. DOI: 10.1021/bm049477j
9. Mei-Chin Chen, Hung-Wen Tsai, Yen Chang, Wei-Yun Lai, Fwu-Long Mi, Chin-Tang Liu, Hen-Sheng Wong, Hsing-Wen Sung. Rapidly Self-Expandable Polymeric Stents with a Shape-Memory Property. DOI: 10.1021/bm7004615
10. Elisa Zini, Mariastella Scandola, Piotr Dobrzynski, Janusz Kasperczyk, Maciej Bero. Shape memory behavior of novel (1-lactide-glycolide-trimethylene carbonate) terpolymers. DOI: 10.1021/bm700773s
11. Ward Small, Pooja Singhal, Thomas S. Wilsona, Duncan J. Maitland. Biomedical applications of thermally activated shape memory polymers. DOI: 10.1039/B923717H
12. Sabine Neuss, Iris Blomenkamp, Rebekah Stainforth, Dagmar Boltersdorf, Marc Jansen, Nick Butz, Alberto Perez-Bouza, Ruth Knüchel. The use of a shape-memory poly(ε-caprolactone)dimethacrylate network as a tissue engineering scaffold. DOI: 10.1016/j.biomaterials.2008.12.027
13. Changchun Min, Wenjin Cui, Jianzhong Bei, Shenguo Wang. Effect of comonomer on thermal/mechanical and shape memory property of L-lactide-based shape-memory copolymers. DOI: 10.1002/pat.865
14. Chien-Shen Yang, Hsi-Chin Wu, Jui-Sheng Sun, Hao-Ming Hsiao, Tzu-Wei Wang. Thermo-induced shape-memory peg-pcl copolymer as a dual-drug-eluting biodegradable stent. DOI: 10.1021/am4032295
15. Xiongjun Yu, Lin Wang, Maotao Huang, Tao Gong, Wenbing Li, Yaling Cao, Daijin Ji, Ping Wang, Jing Wang, Shaobing Zhou. A shape memory stent of poly(ε-caprolactone-co-DL-lactide) copolymer for potential treatment of esophageal stenosis. DOI: 10.1007/s10856.011.4475.4
16. Wolfgang Wagermaier, Thomas Zander, Dieter Hofmann, Karl Kratz, U. Narendra Kumar, Andreas Lendlein. In situ x-ray scattering studies of poly(ε-caprolactone) networks with grafted poly(ethylene glycol) chains to investigate structural changes during dual- and triple-shape effect. DOI: 10.1002/marc.201000122
17. Christopher M. Yakacki, Ken Gall. Shape-Memory Polymers for Biomedical Applications. DOI: 10.1007/12.2009.23
18. Y. S. Wong, Y. Xiong, S. S. Venkatraman. Shape memory in un-cross-linked biodegradable polymers. DOI: 10.1163/156856208783432516
19. Liang Xue, Shiyao Dai, Zhi Li. Synthesis and characterization of elastic star shape-memory polymers as self-expandable drug-eluting stents. DOI: 10.1039/C2JM15918J
20. Yu Xiao, Lin Wang, Xiaotong Zheng, Tao Gong. Crosslinked poly(ε-caprolactone)/poly(sebacic anhydride) composites combining biodegradation, controlled drug release and shape memory effect. DOI: 10.1016/j.compositesb.2010.07.001
21. Bioresorbable Scaffolds. From Basic Concept to Clinical Application. Edited by Yoshinobu Onuma & Patrick W. J. C. Serruys. CRC Press, 2017. ISBN 9781498779746

What is claimed is:

1. A biodegradable self-expanding stent, the stent comprising:
 a plurality of struts made of a polymer and arranged into a closed-cell structure, the closed-cell structure arranged into a tubular shape;
 wherein a ratio of an inner diameter of the stent before crimping and to the inner diameter of the stent after crimping is between 3:1 and 5:1, and
 wherein the struts have a decreased width or thickness in places of minimum mechanical stress compared to curved portions of the struts.

2. The stent of claim 1, which an outer diameter of the stent before crimping is between about 0.25 mm and about 40 mm.

3. The stent of claim 1, wherein a length of the stent is between 5 mm and 250 mm.

4. The stent of claim 1, wherein an average molecular weight of the polymer is 20-600 kDa.

5. The stent of claim 1, wherein the average molecular weight of the polymer is 100-400 kDa.

6. The stent of claim 1, wherein a polydispersity index of the polymer is 1.3-2.5.

7. The stent of claim 6, wherein the polydispersity index of the polymer is 1.5-2.0.

8. The stent of claim 1, wherein a glass transition temperature of the polymer is over 37 degrees Celsius.

9. The stent of claim 8, wherein the glass transition temperature of the polymer is over 42 degrees Celsius.

10. The stent of claim 1, wherein the polymer is obtained by copolymerization of monomers selected from L-lactide, D-lactide, D,L-lactide, meso-lactide, glycolide, c-caprolactone, trimethylene carbonate, p-dioxanone and compounds comprising functional groups capable of photopolymerization.

11. The stent of claim 10, wherein the polymer is a copolymer of L,L-lactide and c-caprolactone.

12. The stent of claim 1, wherein a width of struts is 0.01-1 mm.

13. The stent of claim 1, wherein a thickness of struts is 0.02-0.5 mm.

14. The stent of claim 1, wherein the struts have an increased width or thickness in places of maximum mechanical stress, compared to linear portions of the struts.

15. The stent of claim 1, wherein struts have elongated perforations in places of minimum mechanical stress.

16. The stent of claim 1, wherein supramolecular structures of the polymer are oriented substantially circularly, when seen in a transversal cross section of the stent.

17. A method of manufacturing a biodegradable self-expanding stent, the method comprising:
- extruding a tube of a polymer material using a rotational extrusion head to provide a substantially circular supramolecular structure of the polymer, when seen in a transversal cross section of the tube;
- annealing the extruded tube;
- laser carving the extruded tube to form a stent comprising a plurality of struts, wherein the struts form a closed-cell structure, and the closed-cell structure is arranged into a tubular form;
- heating the stent to a temperature above a glass transition temperature of the polymer material, sharply crimping the stent uniformly over entire outer surface thereof, and subsequently quenching the stent to provide a ratio of the stent inner diameter values before and after crimping in a range of 3:1 to 5:1; and
- placing the quenched stent on a delivery means or in a delivery means.

18. The method of claim 17, wherein the quenching is performed at a temperature of minus 20 degrees Celsius or lower after the crimping.

* * * * *